US007811589B2

(12) United States Patent
Murphy et al.

(10) Patent No.: US 7,811,589 B2
(45) Date of Patent: Oct. 12, 2010

(54) **METHOD FOR STIMULATING IMMUNE RESPONSE AGAINST *MORAXELLA CATARRHALIS***

(75) Inventors: Timothy F. Murphy, E. Amherst, NY (US); Alan J. Lesse, E. Amherst, NY (US); Charmaine Kirkham, E. Aurora, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 12/345,430

(22) Filed: Dec. 29, 2008

(65) Prior Publication Data

US 2009/0169577 A1 Jul. 2, 2009

Related U.S. Application Data

(60) Provisional application No. 61/017,330, filed on Dec. 28, 2007.

(51) Int. Cl.
*A61K 39/02* (2006.01)

(52) U.S. Cl. ............... 424/251.1; 424/190.1; 424/193.1

(58) Field of Classification Search ....................... None
See application file for complete search history.

(56) References Cited

U.S. PATENT DOCUMENTS

| | | | |
|---|---|---|---|
| 6,673,910 B1 * | 1/2004 | Breton | 536/23.1 |
| 2004/0029129 A1 * | 2/2004 | Wang et al. | 435/6 |

FOREIGN PATENT DOCUMENTS

WO WO/02/077183 * 10/2002

OTHER PUBLICATIONS

Ruckdeschel et al.; Mining the *Moraxella catarrhalis* Genome: Identification of Potential Vaccine Antigens Expressed during Human Infection; Infection and Immunity, Apr. 2008, vol. 76, No. 4; pp. 1599-1607.

* cited by examiner

*Primary Examiner*—Jennifer E Graser
(74) *Attorney, Agent, or Firm*—Hodgson Russ LLP

(57) ABSTRACT

Provided is a method for stimulating in an individual an immune response against *M. catarrhalis*. The method is performed by administering to an individual a composition that contains at least one isolated *M. catarrhalis* protein in an amount effective to stimulate an immune response against *M. catarrhalis* in the individual. The *M. catarrhalis* proteins used in the method of the invention are *M. catarrhalis* proteins Msp22, Msp75, Msp78, Protein 28, Protein 99, Protein 238, and combinations thereof.

12 Claims, 12 Drawing Sheets

No. of cells counted
0
40
80
120
Fluorescence
0
10
100
1,000
10,000
a
b
c
No. of cells counted
0
40
80
120
Fluorescence
0
10
100
1,000
10,000
a
b
c

Figure 12.

Msp 78 Protein
MALKKITGNLSIRRTHMSKPTLIKTTLICALSALMLSGCSNQADKAAQPKSSTVDAAA
KTANADNAASQEHQGELPVIDAIVTHAPEVPPPVDRDHPAKVVVKMETVEKVMRLA
DGVEYQFWTFGGQVPGQMIRVREGDTIEVQFSNHPDSKMPHNVDFHAATGPGGGAE
ASFTAPGHTSTFSFKALQPGLYVYHCAVAPVGMHIANGMYGLILVEPKEGLPKVDKE
YYVMQGDFYTKGKYGEQGLQPFDMEKAIREDAEYVVFNGSVGALTGENALKAKVG
ETVRLFVGNGGPNLTSSFHVIGEIFDKVHFEGGKGENHNIQTTLIPAGGAAITEFKVDV
PGDYVLVDHAIFRAFNKGALGILKVEGEENHEIYSHKQTDAVYLPEGAPQAIDTQEA
PKTPAPANLQEQIKAGKATYDSNCAACHQPDGKGVPNAFPPLANSDYLNADHARAA
SIVANGLSGKITVNGNQYESVMPAIALSDQQIANVITYTLNSFGNKGGQLSADDVAK
AKKTKPN (SEQ ID NO:5)

Msp 75 Protein
MNQPTNQSTTQPSSIPLNCPNLLKQACLIDGEWVGADSGETIAVTNPFTGDVLGTIPSL
SKQTVLNAVECADAAQESWANTTASERAKLLHAWADLIDTHKEDLALIMTYEQGKP
ITESQGEIDYANSFIRWFADEGKRIYGDVIPSTNQSLRYVVLKQPVGVCAAITPWNFPS
AMIARKAAPALAAGCTMIIKPAVETPFSALALGYLAKQAGIPKGVLQIVTGKSSVVGE
VLTKDPRIHKLSFTGSTEVGRVLMEQCASTIKKLSMELGGNAPFIVFDDADLEKAAEG
LIASKYRNAGQTCVCANRIYVQSSIKDEFLAKFKQKVEVLKVGNGADEATDIGPLINQ
QALKKVQALLDDALNKGATLITGGVPHDASQLSFTPTVISDITDEMDLAHEEIFGPIAP
IMTFEDEKEVIHRANDTIYGLAAYFYTQSHARAWRVSEALEYGMVGQNTGLLSTEV
APFGGVKQSGFGREGSKYGIEEYITTKYWCMDISE (SEQ ID NO:3)

Msp22 Protein
MFHKITLAAACFMTVILAGCNSSGTATANNPQVEDRAKLMKDWRHANEGMKAMIE
DPSRFDAITFKERADFIADTNATMWVHFEGEMAQGGHAKDEIWTDPEGFKTKIEAFT
SSINALALAASEAASAADVEASYGEMASQCGSCHKAYKKK (SEQ ID NO:1)

Protein 238
MKTVSKSLLGLASITLTASLSMNAQAGNSPANIDNVLQQLTTQHNNASSLVKSVRQP
ASLALNSPMIAQSTKSKKTDEDIPVLDRLTAVASSTVNKFKQNGIASWYGRQFHGRK
TASGETFDMNALTAAHSSLPMNCHVRVTNRDNGKSVVVKINDRPKTNRVLDLSYGA
AQAIGMTGNVGNVTIERID (SEQ ID NO:11)

Protein 99
MKLLKITLFASILGSATFSHSLSAIANTRFETIDITTLTNQAARGDYHAQFFLAKRLQK
GEGVTKDASKAVYWYTRAAEKNIAPAQLNLGIMYLRGEGVRADIATGRAWLEKAA
NLGDNRASYALAMIDEQQQRLVDAYKWYDLSAREGMLDDNVRNRAKVKVSQLAL
NLSSSEIESAKRSANAWFLNQ (SEQ ID NO:9)

Protein 28
MIKPFATLATVACVTLAGCTKEETSTQTTAPAQPSQKSIVIATEAAYPPFNDTDASGQI
IGFDVDVMNALCAEMHAHCQIIAQDWDGLIPSLLAGKYDAIIAGMSITPERQAQVDF
SDSYFSNTIVWLAKSDGSFDPNNITNQTLASQRGTTGAAYITEKYDGKDGNRVQLHD
TYTNAYLDTKAGRNHAVMAEKVSAIDWLKQEGNGEFGLIGEEIDNNDHLGIAVRKG
DSLKAEFDAALAKIKESGKLAEIEKAHFQSDTF (SEQ ID NO:7)

METHOD FOR STIMULATING IMMUNE RESPONSE AGAINST *MORAXELLA CATARRHALIS*

This application claims the benefit of U.S. Provisional application No. 61/017,330 filed Dec. 28, 2007, the disclosure of which is incorporated herein by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is M_Cat_Sequence_Listing.txt. The text file is 25 KB, was created on Dec. 29, 2008, and is being submitted electronically via EFS-Web, concurrent with the filing of this specification.

FIELD OF THE INVENTION

The present invention relates generally to *Moraxella catarrhalis* (*M. catarrhalis*) infection, and more specifically to methods for stimulating an immune response against *M. catarrhalis* bacteria.

BACKGROUND OF THE INVENTION

*M. catarrhalis* is an aerobic, gram-negative diplococcus that is an important respiratory tract pathogen in humans. *M. catarrhalis* annually causes 4 to 5 million of the total 25 million episodes of acute otitis media in the U.S. (Murphy, T. F. 2005. Expert Rev Vaccines 4:843-853). Between $3.8 and $5.7 billion dollars are spent annually in the U.S. alone on healthcare for children with otitis media (American Academy of Pediatrics 2004. Pediatrics 113:1451-1465; Brixner, D. I. 2005. IAm J Manag Care 11:S202-210). A subset of children is otitis prone, experiencing recurrent acute and chronic otitis media, which are associated with delayed speech and language development. Therefore, individuals who suffer from otitis media represent a group that would benefit from an effective therapeutic and/or prophylactic method that could be used against *M. catarrhalis*. However, there is currently no such method available.

*M. catarrhalis* is also a cause of exacerbations of chronic obstructive pulmonary disease (COPD). *M. catarrhalis* infection is the second most common cause of exacerbations of COPD after nontypeable *Haemophilus influenzae*, and COPD affects 24 million Americans, with *M. catarrhalis* causing 2 to 4 million exacerbations annually (Mannino, D. M. 2002. Chest 121:121 S-126S; Murphy, T. F. et al. Am J Respir Crit. Care Med 172:195-199). Overall, COPD is the 4th leading cause of death in the U.S. costing an estimated $32.1 billion in direct and indirect health care costs annually (Mannino, D. M., and A. S. Buist. 2007. Lancet 370:765-773). Adults with COPD represent a second group that would benefit from an effective therapeutic and/or prophylactic method that could be used against *M. catarrhalis*. Such method would reduce the morbidity, mortality, and financial costs associated with COPD. The present invention addresses the need for methods for therapeutic and/or prophylactic approaches to prevent and/or treat disorders caused by *M. catarrhalis* infection.

SUMMARY OF THE INVENTION

The present invention provides a method for stimulating in an individual an immune response against *M. catarrhalis*. The method comprises administering to an individual a composition comprising at least one isolated *M. catarrhalis* protein in an amount effective to stimulate an immune response against *M. catarrhalis* in the individual. The *M. catarrhalis* proteins used in the method of the invention are *M. catarrhalis* proteins Msp22, Msp75, Msp78, Protein 28, Protein 99, Protein 238, and combinations thereof. The amino acid sequences of these proteins are presented in FIG. 12.

The immune response stimulated in the individual may be a prophylactic or a therapeutic immune response. The stimulated immune response may comprise stimulation of an *M. catarrhalis* specific humoral immune response, such as by generation of antibodies in the individual against *M. catarrhalis*. The stimulated immune response may also comprise an *M. catarrhalis* specific cell-mediated immune response. In one embodiment of the invention, performing the method of the invention results in an enhanced rate of *M. catarrhalis* bacterial clearance from the lungs of an individual to whom the composition is administered.

DESCRIPTION OF THE FIGURES

FIG. 12 provides the amino acid sequences of Msp22, Msp75, Msp78, Protein 28, Protein 99, Protein 238.

DETAILED DESCRIPTION OF THE INVENTION

The present invention provides a method for stimulating in an individual an immune response against *M. catarrhalis*. The method comprises administering to the individual a composition comprising at least one isolated *M. catarrhalis* protein in an amount effective to stimulate an immune response against *M. catarrhalis* in the individual.

The *M. catarrhalis* proteins used in the present invention are *M. catarrhalis* proteins referred to herein as Msp22, Msp75, Msp78, Protein 28, Protein 99, Protein 238, and includes combinations thereof.

Figure 1:
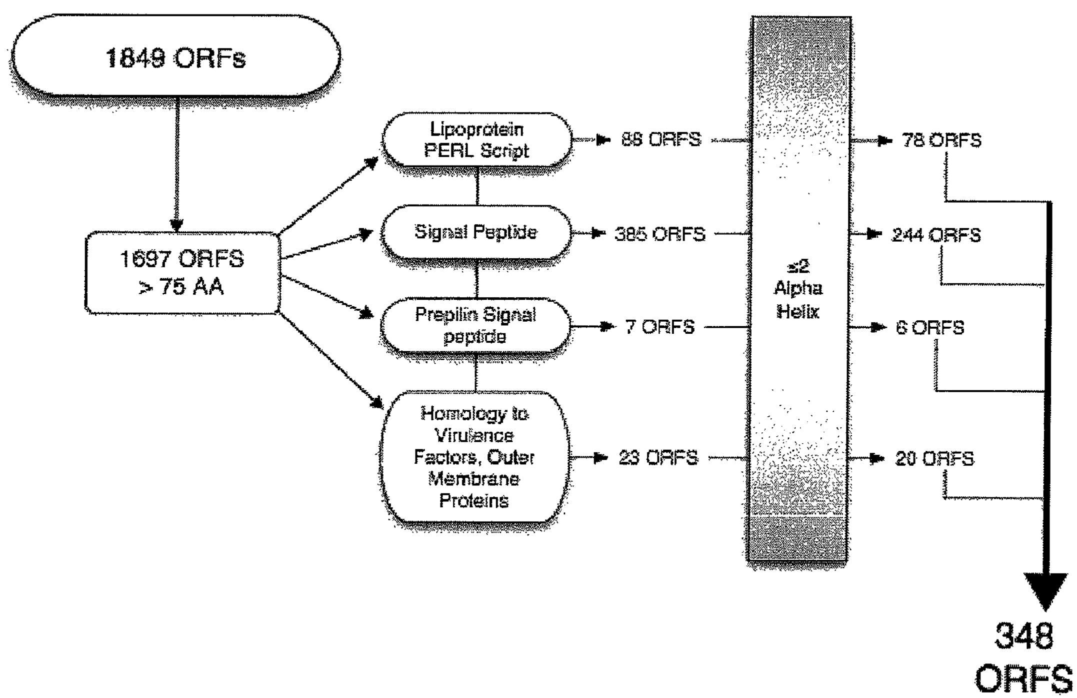
FIG. 1 provides a flow chart of genomic sequence analysis for potential surface proteins. Open reading frames based on analysis of unannotated genome sequence of *M. catarrhalis* ATCC 43617.

The amino acid sequence of Msp22 is provided as SEQ ID NO: 1. The cDNA sequence encoding mMsp22 is provided as SEQ ID NO:2. The amino acid sequence of Msp75 is provided as SEQ ID NO:3. The cDNA sequence encoding Msp75 is provided as SEQ ID NO:4. The amino acid sequence of Msp78 is provided as SEQ ID NO:5. The cDNA sequence encoding Msp78 is provided as SEQ ID NO:6. The amino acid sequence of Protein 28 is provided as SEQ ID NO:7. The cDNA sequence encoding Protein 28 is provided as SEQ ID NO:8. The amino acid sequence of Protein 99 is provided as SEQ ID NO:9. The cDNA sequence encoding Protein 99 is provided as SEQ ID NO: 10. The amino acid sequence of Protein 238 is provided as SEQ ID NO:11. The cDNA sequence encoding Protein 238 is provided as SEQ ID NO:12. It will be recognized by those skilled in the art that the invention includes all nucleic sequences encoding the *M. catarrhalis* proteins disclosed herein, and that variations in amino acid sequences of the proteins that do not adversely affect the capability of the proteins to stimulate an immune response against *M. catarrhalis* in an individual according to the method of the invention are also contemplated The *M. catarrhalis* proteins of the present invention were discovered using a combination of bioinformatic and experimental strategies to identify putative open reading frames (ORFs) that encode novel proteins located on the surface of *M. catarrhalis*. Such surface proteins are preferable for use in stimulating immune responses that would be prophylactic and/or therapeutic for *M. catarrhalis* infection. In addition to exposure on the bacterial surface, preferable immunogenic *M. catarrhalis* proteins have sequence conservation among strains and are expressed during human infection. We adopted an approach to ORF discovery that included experimental analysis in combination with cell location predictions based on sequence homology to structural or functional motifs found in other proteins that are present on bacterial cell surfaces. We employed a series of distinct experimental techniques in arriving at the present invention because it is difficult to correctly predict the cellular location of proteins based solely on homology to structural or functional motifs found in other cell surface proteins. For example, outer membrane protein (OMP) P4 of *Haemophilus influenza* was predicted to be localized to the cytoplasm or in the cytoplasmic membrane, but is now known to be a located on the bacterial surface (Reilly T J, et al. J Bacteriol 1999; 181:6797-805; Reilly T J, et al. FEBS Lett 2001;494:19-23. Penicillin binding protein 3 (PBP 3) of *Neisseria gonorrhoeae* was long been thought to be located exclusively in the cytoplasmic membrane, but surprisingly, this protein is located on the bacterial surface (Shafer et al. Mol Microbiol 1991;5:1097-103). Likewise, Alpha-2,3-sialyltransferase of *N. gonorrhoeae* is a lipooligosaccharide synthesis enzyme and was believed to be located in the cytoplasm due to its function, but has now been identified as a surface exposed outer membrane protein (Shell D M, et al. Infect Immun 2002;70:3744-51). An overview of the initial discovery strategy is depicted in FIG. 1. Specific details of the strategy presented in FIG. 1 are described in Examples 1 and 2 below. Of the 348 candidate ORFs, we describe herein six proteins encoded by six of the candidate ORFs. It is expected that any one, or any combination of these proteins can be used in compositions for stimulating an immune response against *M. catarrhalis*. In this regard, the compositions used in the method of the present invention comprise at least one isolated *M. catarrhalis* protein. By "isolated *M. catarrhalis* protein" it is meant that the protein is separated from its natural environment.

Isolated proteins used in the method of the invention may be obtained by methods known to those skilled in the art, such as by isolation of the proteins from *M. catarrhalis* cultures, or by producing the proteins recombinantly from expression vectors inserted into cells using conventional techniques, culturing the cells under conditions whereby the proteins are synthesized by the cells, and isolating the proteins from the cells according to established procedures.

The isolated *M. catarrhalis* proteins may be purified to any desired degree of purification. Methods for protein purification are well known in the art and are applicable to preparing purified *M. catarrhalis* proteins for use in the present invention. In various embodiments, the *M. catarrhalis* proteins used in the invention may be partially purified, substantially purified, or fully purified.

The isolated *M. catarrhalis* proteins used in the invention are considered to comprise an anti-*M. catarrhalis* antigenic component of the composition that is administered to the individual. In this regard, the anti-*M. catarrhalis* antigenic component of the composition may comprise one or more *M. catarrhalis* proteins, or may consist essentially of one or more *M. catarrhalis* proteins, or may consist of one or more *M. catarrhalis* proteins.

Compositions comprising the proteins, such as pharmaceutical compositions for administration to individuals, may be prepared by mixing the proteins with any suitable pharmaceutically acceptable carriers, excipients and/or stabilizers to obtain pharmaceutical compositions. Some examples of acceptable carriers, excipients and stabilizers suitable for combining with the proteins can be found in: *Remington: The Science and Practice of Pharmacy* (2005) 21st Edition, Philadelphia, Pa. Lippincott Williams & Wilkins.

The compositions of the invention may be administered in combination with any suitable adjuvant or adjuvant combination. In one embodiment, the adjuvant may be cholera toxin. In another embodiment, the adjuvant may be Freund's incomplete adjuvant.

It is expected that the compositions used in the method of the invention may be administered to any mammal to stimulate an immune response against *M. catarrhalis* bacteria. In one embodiment, the mammal is a human.

The method can be performed by administering the composition to the individual via any acceptable method of delivery which enables the composition to stimulate an immune response to *M. catarrhalis* bacteria in the individual. Examples of acceptable administration routes include but are not limited to subcutaneous, intramuscular, intravenous, intradermal, intranasal, oral and inhalation administrations. In one embodiment, the compositions are administered subcutaneously. In another embodiment, the compositions are administered intransally.

It will be recognized by those of skill in the art that the form and character of the particular dosing regimen employed in the method of the invention will be dictated by the route of administration and other well-known variables, such as the size of the individual and the stage of the infection. It is generally considered that the amount of protein administered will range from approximately 100 micrograms to milligrams. Accordingly, in view of the present invention, one skilled in the art can determine an amount of isolated *M. catarrhalis* protein that is effective to stimulate an immune response against *M. catarrhalis* for any particular individual in need of such a stimulated immune response.

The immune response stimulated in the individual by the method of the invention may be a prophylactic or a therapeutic immune response. The stimulated immune response may comprise an *M. catarrhalis* specific humoral immune response, an *M. catarrhalis* specific cell-mediated response, or both. The humoral response may be a systemic response, a mucosal response, or both.

In one embodiment, the stimulated immune response comprises generation of antibodies in the individual that are specific to *M. catarrhalis* bacteria via specific binding of the antibodies to the protein to the bacteria. The antibodies generated via stimulation of an immune response in the individual may by present in a variety of bodily fluids/tissues. Non-limiting examples of fluids in which the stimulated antibodies may be present include serum and sputum.

Stimulation of an immune response in an individual can be determined according to well known techniques. In one embodiment, stimulation of an immune response can be determined by detecting an increase in antibodies that recognize *M. catarrhalis* bacteria in an individual to whom a composition of the invention has been administered. An increase in antibodies in the individual that recognize *M. catarrhalis* bacteria can be detected using a variety of well known techniques, non-limiting examples of which include ELISAs and bactericidal assays. In one embodiment, an increase in antibodies to *M. catarrhalis* bacteria can be measured by determining an increase in antibodies to the isolated *M. catarrhalis* protein used in the composition administered to the individual.

The antibodies generated in the individual may comprise any antibody isotype. In various embodiments, the antibodies may be IgG antibodies, IgA antibodies, or combinations thereof.

In another embodiment, stimulation of an immune response to *M. catarrhalis* bacteria in an individual can be determined by detecting an enhanced rate of *M. catarrhalis* bacterial clearance from the lungs of an individual to whom the composition is administered, relative to the rate of *M. catarrhalis* bacterial clearance from the lungs of an individual to whom the composition has not been administered.

The compositions of the invention may be administered in a single dose or in more than one dose. For example, in one embodiment, the composition may be administered as several doses over a period of time, such as by providing an initial administration, and subsequent administrations intended to boost the stimulation in immune response. The compositions of the invention may also be administered prior to, concurrently, or subsequent to conventional anti-bacterial treatments, such as antibiotic treatments.

The following Examples are meant to illustrate, but not limit the invention.

EXAMPLE 1

This Example provides and description of the Materials and Methods used to obtain the data presented in Example 1 through Example 8.

Sequence analysis. The genome of strain ATCC 43617 was analyzed using 41 contigs deposited in the GenBank database (Accession numbers AX067426 through AX067466). GeneMarkS was used to identify open reading frames (ORFs) from the genome sequence (Besemer, Jet al. 2001. Nucleic Acids Res. 29:2607-2618). Potential lipoproteins were identified using a PERL script based on sequences described in the Prosite database (www.us.expasy.org). SignalP was used to identified ORFs with signal sequences characteristic of membrane proteins and secreted proteins (Emanuelsson, et al. 2007. Nat. Protoc. 2:953-971). Type IV signal peptides were identified with an in-house PERL script. Searches of annotations from the April 2003 Genbank protein database revealed 13,536 bacterial proteins with the expressions outer membrane protein, secreted protein, and virulence. These were combined with 199 annotated bacterial lipoproteins from the DOLOP database (Altschul, et al. 1997. Nucleic Acids Res. 25:3389-3402; Madan et al. 2002. Bioinformatics 18:641-643). The combined annotated proteins were converted to a BLAST searchable database using formatdb (www.ncbi.nlm- .nih.gov/blast/download.shtml). Predicted ORFs were compared to this database and proteins with e values less than $1\times10^{-30}$ were identified.

Construction of microarray. Primers were made for each of the 348 ORFs predicted by sequence analyses. PCR was performed using template DNA from *M. catarrhalis* strain 43617 to generate products that were spotted on a microarray. Prior to microarray construction, each PCR product was confirmed to be the correct size by agarose gel electrophoresis. Microarray construction and hybridizations were done at the Roswell Park Cancer Institute (RPCI) Microarray and Genomics facility. The PCR products were resuspended in 20 μl of 25% DMSO and rearrayed into 384-well plates. Slides were then printed using MicroSpot 10K split pins and a MicroGrid II TAS arrayer (BIOROBOTICS, Inc.). The ORF products had ~150 μm diameter spots with 300 μm center to center spacing. During the print run the environment was controlled for humidity, temperature, and dust. Each ORF product was printed 12 times on amino-silanated glass slides (Schott Nexterion type A). Each print run contained amplicons corresponding to 3 genes (genes encoding outer membrane proteins CD, E and G1b) that show >95% identical sequence to the reference strain and were spotted ~600 times. PCR products of irrelevant genes from *H. influenzae* were included as negative controls. The printed slides dried overnight and were UV-crosslinked (500 mJ) in a Stratalinker 2400 (STRATAGENE). The slides were hybridized without additional treatment. No indication of DNA loss from the spots was detected at any stage when hybridization in formamide buffers at 55° C. was performed (via DAPI staining).

Bacterial strains and culture conditions. *M. catarrhalis* strains 43617, 25238, and 25240 were obtained from the American Type Culture Collection (Manassas, Va.). Isolate O35E was provided by Dr. Eric Hansen. Strains M2, M9, M10 and M11 were sputum isolates from Houston, Tex. given by Dr. Daniel Musher. Strains 14, 21, 23, 27, and 48 were sputum isolates from Johnson City, Tenn. obtained from Dr. Steven Berk. Strains 435, 565, 636, and 1089 were sputum isolates from Birmingham, UK, provided by Dr. Susan Hill. Middle ear fluid isolates 2951, 3584, 4223, 4608, 5191, 7169, and 8184 were provided by Dr. Howard Faden. Strains 6P29B1 and 7P94B1 were sputum isolates obtained from adults in our COPD study clinic. Chemically competent *Escherichia coli* strains TOP10 and BL21(DE3) were obtained from INVITROGEN.

*M. catarrhalis* strains were grown on brain heart infusion (BHI) plates at 37° C. with 5% $CO_2$ or in BHI broth with shaking at 37° C. *E. coli* strains were grown on Luria-Bertani (LB) plates, LB broth, or in terrific broth (TB) at 37° C. supplemented with the appropriate antibiotics (MoBio Laboratories, Carlsbad, Calif.).

Competitive hybridization of genomic DNA. Genomic DNA was labeled using the fluorescent nucleotide analog Cy5 (strain 43617) and Cy3 (test strains). One μg of genomic DNA was random primer labeled using a BioPrime DNA labeling kit (INVITROGEN, Inc.) for 3 hours at 37° C. with the appropriate dye (Cy3 or Cy5). After ethanol precipitation, the probes were resuspended in $H_2O$, combined, and purified of unincorporated Cy dye by passage over a Qiagen spin column. The labeled probes were dried and stored at −20° C. until hybridization.

Hybridization to the microarrays was conducted under controlled conditions. The probes were combined and resuspended in 110 μl of hybridization solution (3.5× standard saline citrate (SSC), 40 μg salmon sperm DNA, 0.25% sodium dodecyl sulfate (SDS)), heated to 95° C. for 5 minutes, and placed on ice. The entire probe was added to the array and hybridization proceeded for 16 h at 55° C. in a GeneTAC hybridization station (GENOMICS SOLUTIONS, INC.). After hybridization, the slide was washed with decreasing concentrations of SSC and SDS, followed by one 0.1×SSC wash, one 95% ethanol rinse, and centrifugal drying for 3 min.

The hybridized slides were scanned using a GenePix 4200A Scanner to generate high-resolution (10 μm) images for both Cy3 and Cy5 channels. Image analysis was performed on the raw image using ImaGene version 4.1 from BIODIVERSITY, Inc.

Each spot was defined by a circular region. The size of the region was programmatically adjusted to match the size of the spot. A buffer region of 2-3 pixels around the spot was ignored. There were another 2-3 pixels outside the buffer region that were considered the local background for that spot. Each spot and its background region were segmented using a proprietary optimized segmentation algorithm that excluded pixels not representative of the rest of the pixels in the region. The background corrected signal for each cDNA was the mean signal of all the pixels in the region minus the mean local background. The output of the image analyses were two tab delimited files, one for each channel, containing all of the fluorescence data.

The output of the image analysis was then processed by an in-house developed program. Spots that were not significantly above background or had a poor coefficient of variation were excluded. For each spot, a ratio was calculated from the background subtracted mean signal of the two channels, one representing the reference strain 43617 and one representing the test strain. The ratios were normalized on the log scale across clones known to have high homology. Replicate measurements were averaged on the log scale. The final $\log_2$ ratio was converted back to a linear ratio.

Reverse transcriptase-PCR. Bacterial RNA was isolated using a QIAGEN RNeasy kit and a Qiashredder column (QIAGEN, Valencia, Calif.) following the manufacturer's instructions, with an additional incubation with RNase-free DNaseI (PROMEGA) for 30 min at 37°. Reverse transcriptase PCR (RT-PCR) was performed using a QIAGEN OneStep RT-PCR kit and RNaseOut inhibitor (INVITROGEN, Carlsbad, Calif.). Primers were designed to amplify ~500-bp fragments of msp75 and msp78 and full size msp22 (Table 1). To exclude the possibility of contaminating DNA, parallel reactions with TaqI DNA polymerase (HotMaster mix; Eppendorf, Hamburg, Germany) were performed. Following amplification, samples were electrophoresed in 1.5% agarose gels and stained with ethidium bromide. For Table 1, restriction enzyme sites are italicized.

TABLE 1

| Gene | Experiment | Direction | Primer Sequence |
| --- | --- | --- | --- |
| msp22 | Clone gene | forward | 5'ATATATAT*CCATGG*AACAGCTAGGGACTGCCACC3' (SEQ ID NO: 13) |

TABLE 1-continued

| Gene | Experiment | Direction | Primer Sequence |
|---|---|---|---|
| msp22 | Clone gene | reverse | 5'TCTCTA*GGATCC*AGAACCACACTGGCTGGCCATTTC3' (SEQ ID NO: 14) |
| msp22 | RT-PCR | forward | 5' AACAGCTAGGGACTGCCACC 3' (SEQ ID NO: 15) |
| msp22 | RT-PCR | reverse | 5' CTTCAGGGTCTGTCCATATCTC 3' (SEQ ID NO: 16) |
| msp75 | Clone gene | forward | 5' ATAT*GGATCC*GCAAGCCTGTTTGATTG 3' (SEQ ID NO: 17) |
| msp75 | Clone gene | reverse | 5' GCGC*GAATTC*TTATTCGCTGATATCC 3' (SEQ ID NO: 18) |
| msp75 | RT-PCR | forward | 5' GATACACACAAGGAAGATTTG 3' (SEQ ID NO: 19) |
| msp75 | RT-PCR | reverse | 5' CATAGATACGGTTGGCACACAC 3' (SEQ ID NO: 20) |
| msp78 | Clone gene | forward | 5' ATAT*GGATCC*AGCGGACAAAGCCGCC 3' (SEQ ID NO: 21) |
| msp78 | Clone gene | reverse | 5'GCGC*GAATTC*TCAGTTTGGCTTGGT 3' (SEQ ID NO: 22) |
| msp78 | RT-PCR | forward | 5' CATTTACCGCACCGGGTCATAC 3' (SEQ ID NO: 23) |
| msp78 | RT-PCR | reverse | 5' CTTCTTGGGTATCAATTGCTTG 3' (SEQ ID NO: 24) |

Expression and purification of recombinant proteins. Selected putative surface proteins were selected for further study based on the data mining strategy above and their sequence conservation among strains. Genes were amplified by PCR from *M. catarrhalis* ATCC 43617 genomic DNA using gene specific primers (SIGMA-GENOSYS, The Woodlands, Tex.) (Table 1). The primers included restriction enzyme sites for Nco1, BamH1, or EcoR1 onto the ends of the amplified genes to allow for directional cloning into either pRSETB (INVITROGEN, San Diego) for msp75 and msp78, or pCATCH for msp22 (Cullen, et al. 2003. Plasmid 49:18-29). Cloning into these vectors resulted in fusion proteins expressing a 6×-His tag under the control of an isopropyl-β-D-thiogalactosidase (IPTG) inducible promoter. Additionally, the pCATCH plasmid was chosen for msp22, a putative lipoprotein, since the plasmid contains *E. coli* lipoprotein signal sequences that encode for attachment of an N-terminal lipid moiety during processing allowing expression of msp22 with an amino terminal lipid.

Amplifications of msp22 were conducted using Taq HiFi polymerase (INVITROGEN) and an Eppendorf Mastercycler Personal Thermal Cycler as follows: 94° C. for 3 min followed by 30 cycles of: 94° C. for 30 s, 55° C. for 30 s, and 68° C. for 90 s. Amplifications for msp 75 and msp 78 were conducted using Vent polymerase (New England Biolabs) as follows: msp75: 94° C. for 3 min followed by 30 cycles of: 94° C. for 30 s, 58° C. for 30 s, and 72° C. for 90 s; msp78: 94° C. for 3 min followed by 30 cycles of: 94° C. for 30 s, 52° C. for 30 s, and 72° C. for 90 s. Aliquots from the PCR were subjected to agarose gel electrophoresis. PCR products were purified using QIAquick PCR Purification Kit (Qiagen, Chatsworth, Calif.) and cloned into either pRSET or pCATCH.

Chemically competent TOP 10 *E. coli* cells were transformed with the recombinant plasmids. Colonies were picked from LB plates containing 30 μg/ml kanamycin (msp22) or 60 μg/ml carbenicillin (msp75 and msp78). Plasmids were confirmed to have the gene insert by PCR and by sequencing at the RPCI Biopolymer Facility.

The recombinant plasmids were purified using a Qiagen plasmid mini purification system using the manufacturer's instructions. The plasmids were transformed into chemically competent *E. coli* BL21(DE3) for expression. To express rMsp22, a 10 ml culture of LB with 60 μg/ml kanamycin was inoculated and allowed to grow overnight at 37° C. with shaking. To express rMsp75 and rMsp78, a 10 ml culture of LB with 100 μg/ml carbenicillin was inoculated and allowed to grow overnight at 37° C. with shaking. The following day, 200 ml of TB containing either 120 μg/ml kanamycin (rMsp22) or 300 μg/ml carbenicillin (rMsp75 and rMsp78) was seeded with the overnight culture and allowed to grow to an $OD_{600}$ of 0.6. Recombinant protein was expressed by adding 1 mM IPTG followed 15 min later by 0.15 mg/ml rifampin. After 4 h at 37° C., cultures were centrifuged at 13,000×g at 4° C. for 20 min.

Cell lysis was performed by adding 8M Urea with 0.1M $NaH_2PO_4$ (pH 8.0) to the bacterial pellet and mixing for 30 min at room temperature. Cleared lysate was obtained by centrifugation at 50,000×g at 4° C. for 20 min. The lysate was then added to TALON $Co^{+2}$ metal affinity resin (BD Biosciences, Palo Alto, Calif.) (pre-washed with 8M urea) by mixing with a nutator at room temperature for 1 h. The lysate and resin were centrifuged at 4° C. for 5 min at 3,000×g. The unbound lysate was saved and the resin was washed four times with lysis buffer. After the final wash, the recombinant proteins were eluted from the resin using 10 column volumes of lysis buffer containing 250 mM imidazole. The resulting supernatant was diluted to a final concentration of 4M urea with 0.5M Tris (pH 8.0).

The resulting diluted supernatant was diafiltrated using an Amicon stirred ultrafiltration cell and a 10,000 molecular weight cutoff filter (Millipore, Bedford, Mass.) against 10 volumes of Buffer Z1 (0.01% zwittergent 3-14, 0.05M Tris, 0.01M $Na_2EDTA$, pH 8.0) under nitrogen Once in Buffer Z1, the protein solution was concentrated to 1 ml using an Amicon Ultra-15 Centrifugal filter unit (Millipore, Bedford, Mass.). Protein concentrations were determined using a BCA protein assay kit (Pierce, Rockford, Ill.).

PCR and sequencing. The same primers and PCR conditions given above were used to amplify the three genes using HotMasterMix (EPPENDORF) in the following 25 isolates of *M. catarrhalis*: O35E, M2, M9, M10, M11, 14, 21, 23, 27, 48, 435, 565, 636, 1089, 2951, 3584, 4223, 4608, 5191, 7169, 8184, 25238, 25240, 6P29B1, and 7P94B1. Sequencing for each of the three genes from 10 clinical isolates was performed at the RPCI Biopolymer facility (isolates O35E, M10, 14, 27, 435, 565, 2951, 8184, 25240, and 7P94B1).

COPD study clinic. The COPD study clinic at the Buffalo Veterans Affairs Medical Center is an ongoing prospective study that was started in 1994. To be included in this study, patients must have had chronic bronchitis as defined by the American Thoracic Society (American Thoracic Society. 1995. Am. J. Respir. Crit. Care Med. 152:S77-S121) and must have been willing to attend the study clinic monthly. Patients with asthma, malignancies, or other immunocompromising illnesses were excluded. Patients were seen monthly and at times when an exacerbation was suspected. At each visit clinical criteria were used to determine whether patients were experiencing an exacerbation or whether they were clinically stable. Additionally at each visit, serum and expectorated sputum samples were collected. Bacteria present in the sputum were identified using standard techniques. Serum, sputum supernatants, and bacteria obtained from sputum cultures were stored at −80° C. These samples were used to analyze human antibody responses to the purified recombinant proteins before and after acquisition and clearance of *M. catarrhalis*. All patient data and material was collected and processed in compliance with Veterans Affairs Western New York Heathcare System IRB guidelines.

Enzyme-linked immunosorbent assay (ELISA). Samples of human serum and sputum were obtained from the COPD study clinic. Thirty-one pre-acquisition and post-clearance sera from adults with COPD who acquired *M. catarrhalis* were studied in ELISAs to detect the development of new IgG antibodies in serum to the protein following clearance of the strain. Pre-acquisition and post-clearance sputum supernatants were similarly studied to detect new IgA antibody responses. The change in antibody level from pre-acquisition to post-clearance samples was calculated using the following formula: % change=[(post OD−pre OD)/pre OD]×100.

ELISAs were carried out by coating the wells of a 96-well microtiter Immunolon 4 plate (THERMO LABSYSTEMS, Franklin, Mass.) with recombinant purified protein. The optimal protein concentrations were determined in preliminary assays in order to optimize conditions. Wells were coated with either 1 μg or 5 μg of protein. Following overnight incubation at room temperature, plates were washed four times with PBST (phosphate buffered saline, 0.5% Tween 20). Plates were then blocked using 5% nonfat dry milk in PBS (MPBS) for 1 hour at room temperature. After washing, primary antibody (i.e. serum or sputum) diluted in MPBS was added to the wells. Starting dilutions were approximately 1:200 for serum samples and 1:100 for sputum supernatants. Two-fold dilutions were done on the plate for each sample, for a total of three dilutions per primary antibody for serum, or two dilutions per primary antibody for sputum. Uncoated and coated control wells received MPBS without primary antibody as negative controls. Plates were incubated at 37° C. for 2 h. After the 2 h incubation, plates were again washed four times with PBST. Secondary HRP-conjugated antibody (1:3000 goat-anti-human IgG or 1:2000 goat-anti-human IgA (KPL, Gaithersburg, Md.)) diluted in MPBS was then added. After incubating at 37° C. for 1 h, plates were washed and developing reagent was added to the wells and allowed to react for 15 minutes in the dark. Color development was stopped using $4NH_2SO_4$. Absorbance at 450 nm was read using a BioRad model 3550-UV microplate reader.

EXAMPLE 2

Identification of ORFs that encode putative surface proteins. The genome of strain ATCC 43617 was analyzed using 41 contigs available in the GenBank database. The unassembled DNA fragments had a total length of 1,913,584 bp, which matched the calculated genome size of 1,750,000 to 1,940,000 bp determined experimentally by pulsed field gel electrophoresis (Nguyen, K. T., et al. Can. J. Microbiol. 45:299-303; (Furihata, K., et al. 1995. Microbiol Immunol 39:745-751). Using the GeneMarkS program, a total of 1849 ORFs of sizes ranging from 42 to 1946 bp were obtained. The minimum length ORF was chosen to be 225 bp, making the smallest encoded protein 75 amino acids. This method yielded 1697 ORFs in the *M. catarrhalis* genome.

Several approaches were used to determine the ORFs likely to encode proteins that are processed to the bacterial surface, as surface exposed proteins would represent potential vaccine antigens. ORFs were analyzed to identify lipoproteins; 88 were identified. SignalP, which detects signal sequences for membrane proteins that are cleaved by both signal peptidase I and II, yielded 385 ORFs. Analyzing the ORFs for prepilin-like protein signal sequences that form part of the type II secretion system generated another 7 ORFs. Use of an annotation-based homology search revealed another 23 ORFs. ORFs that were predicted to contain 2 or more regions of α-helix were determined to most likely be located in the cytoplasmic membrane and were therefore excluded. FIG. 1 shows a flow chart of the strategy that resulted in predicting 348 ORFs that encode putative surface exposed proteins.

EXAMPLE 3

Analysis of putative genes for sequence conservation. The 348 ORFs found by sequence analyses were amplified by PCR from strain 43617 template DNA and the products were spotted on a microarray. Ten genes that encode previously identified outer membrane proteins were studied to optimize conditions (UspA1, UspA2, TbpA, TbpB, CopB, LbpA, OMP CD, OMP E, OMPG1a, and OMP G1b). These 10 genes were predicted to be potentially surface localized by genome analysis. Genomic DNA of the homologous 43617 strain was labeled with Cy5 and genomic DNA from 4 different competing strains (25240, O35E, 4223, 25238) were labeled individually with Cy3. These strains were selected because the sequences of the 10 test genes are known for these strains and thus could be used as controls when analyzing the results. Microarrays were probed simultaneously with DNA from the reference strain (43617) and DNA from each of the 4 test strains individually and the red/green ratio was determined to assess the sequence similarity for each ORF compared to the reference strain. As controls, 50 PCR reactions each were performed to amplify the genes that encode OMP CD, E, and G1b yielding 150 spots with greater than 95% homology between strain 43617 and test strains for normalization of data.

To identify conserved genes among strains, competitive hybridizations using genomic DNA of 12 strains of *M. catarrhalis* of diverse geographic and clinical origin were individually performed against genomic DNA from the sequenced strain (strain 43617) used to construct the microarray. A cutoff of greater than a linear ratio of 0.8 between the strain 43617 and each of the 12 clinical strains was used to determine which genes encoded highly conserved proteins. A total of 147 ORFs were identified as showing a signal ratio of >0.8 between strain 43617 and the competing strain for all 12 strains studied, suggesting sequence conservation of these genes among strains. Six genes from the 147 ORFs were chosen to for additional analysis. These genes were designated *Moraxella* surface proteins (Msp) msp22, msp75, and msp78, with the number identifier corresponding to the molecular weight of the predicted protein as determined by gel mobility assay. Proteins designated Protein 28, Protein 99 and Protein 238 were also selected for further study.

Figure 2:
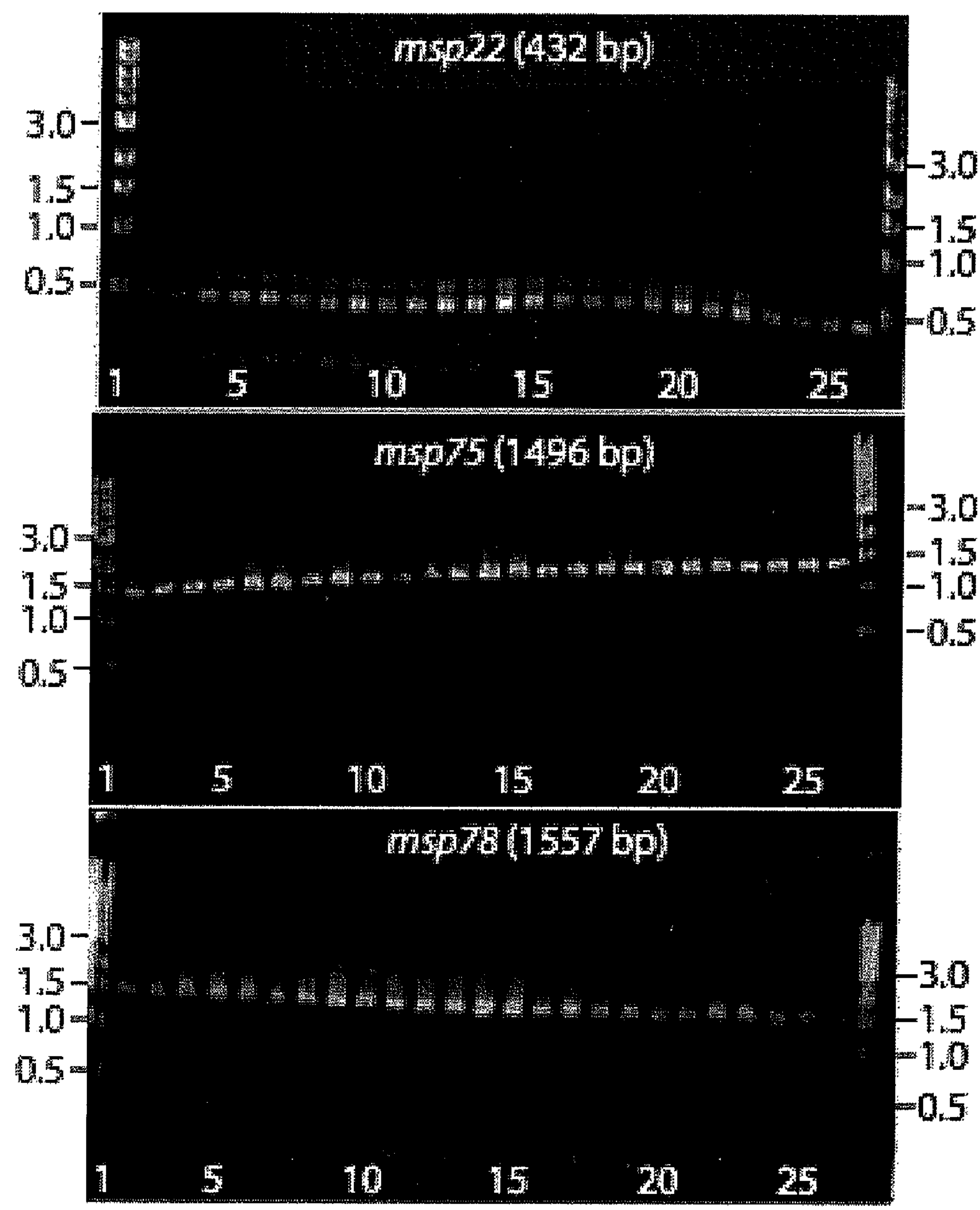
FIG. 2 provides a photographic representation of ethidium bromide stained agarose gels showing amplicons from PCR reactions with primers for genes as noted. Templates were genomic DNA of 25 isolates of *M. catarrhalis*. Lane 1=standard; 2=O35E; 3=M10; 4=M11; 5=14; 6=21; 7=23; 8=27; 9=M9; 10=48; 11=M2; 12=435; 13=565; 14=636; 15=1089; 16=2951; 17=3584; 18=4223; 19=4608; 20=5191; 21=7169; 22=8184; 23=25238; 24=25240; 25=6P29B1; 26=7P94B1; 27=standard. Molecular mass standards as noted in kilobases.

To further assess the sequence conservation of three of the genes identified by competitive hybridization of the microarray, primers corresponding to the genes of interest were designed. The 3 genes (msp22, msp75, and msp78) were amplified by PCR from 25 clinical isolates of *M. catarrhalis*, including the 12 isolates studied by competitive hybridization of the microarray. Primers were based on *M. catarrhalis* strain ATCC 43617, the same strain used for microarray construction. All three genes were present in 25 of 25 clinical isolates tested (FIG. 2). Additionally, each of the PCR products was the expected size for each gene. This result indicated that each of the 3 genes was present in all strains and there was no variation in length of these three genes among the diverse strains examined.

To further evaluate sequence conservation of the genes among strains, the sequence of the entire gene for each of the three genes was determined from 10 clinical isolates (O35E, M10, 14, 27, 435, 565, 2951, 8184, 25240, and 7P94B1). Gene sequences were translated and amino acid homology calculations between strains of *M. catarrhalis* for each gene were done using MacVector (ACCELERYS). The amino acid sequences of each of the 3 genes were 97 to 99% identical among the 10 strains (Table 2). Without intending to be bound by any particular theory, it is believed that genes msp22, msp75, and msp78 are highly conserved among strains of *M. catarrhalis*.

referred to as cytochrome_C__2). Msp22 has the characteristic CxxCH motif at amino acids 142-146 that is associated with heme attachment, although in other Gram-negative bacteria, these cytochromes may be involved with iron and other divalent cation transport. The genes downstream on the complementary strand have significant homology to coproporphyrinogen III oxidase and GTP cyclohydrolase II. This arrangement of a cytochrome, coproporphyrinogen oxidase, and GTP cyclohydrolase is syngeneic to the genome sequence found in *Psychrobacter* sp. PRwf-1, a member of the Family Moraxellaceae, along with the genera *Acinetobacter, Moraxella, Alkanindiges*, and *Enhydrobacter.*

Msp75 is predicted to have 499 amino acids and has high homology to succinic semialdehyde dehydrogenase. The protein was identified for study in the algorithm through BLASTP homology with a region of chromosome of *Agrobacterium tumefaciens* that is associated with virulence. Localization in the cell is predicted to be in the cytoplasm by psortB.

Msp78, containing a signal sequence, has high similarity and identity to an anaerobically induced nitrate reductase. Homologues of this protein have been identified as outer membrane proteins. psortB localizes the protein to the periplasm but also notes that the protein has characteristics of a membrane protein. The protein has multiple pfam domains identified including a multicopper oxidase motif, cytochrome c motif, and copper binding domains.

We also determined that Protein 28 has 100% identify between strains, is a putative surface protein and is similar to an extracellular solute binding ABC transporter. Protein 99 is a also a putative surface protein, has high identity across strains, and it contains Sell -like repeats. Protein 238 also has high identity among strains and has homology with rare lipoprotein A family proteins, although Protein 238 does not itself appear to be a lipoprotein.

TABLE 2

| Gene | Size bp | Size kDa | Isoelectric point | Amino Acid Homology Between Strains of *M. catarrhalis* | Surface Location Predictor | Amino Acid Sequence Homologues (% Identity/% Similarity) |
|---|---|---|---|---|---|---|
| msp22 | 432 | 21.6 | 5.11 | 99% | Lipoprotein | Cytochrome c, class II (*Psychrobacter* sp.) (36%/53%) |
| msp75 | 1497 | 74.9 | 4.83 | 97% | Leader, Membrane | Succinic semialdehyde dehydrogenase (*Psychrobacter* sp.) (73%/85%) |
| msp78 | 1557 | 77.8 | 5.89 | 99% | Leader | Outer membrane nitrite reductase (*Neisseria* sp.) (80%/90%) |

EXAMPLE 4

Characterization of genes. To gain insight into the possible function of Msp22, Msp75, and Msp78, BLASTP homology searches were performed. Table 2 shows a summary of the characteristics for each of the proteins based on BLASTP searches. Msp22, a putative lipoprotein, has significant homology to cytochrome c'. Msp22 is predicted to contain 152 amino acids and has conserved cytochrome c' domain architecture with significant homology to COG3903, which includes the pfam PFO1322, or the cytochrome c' family (also

EXAMPLE 5

Figure 3:
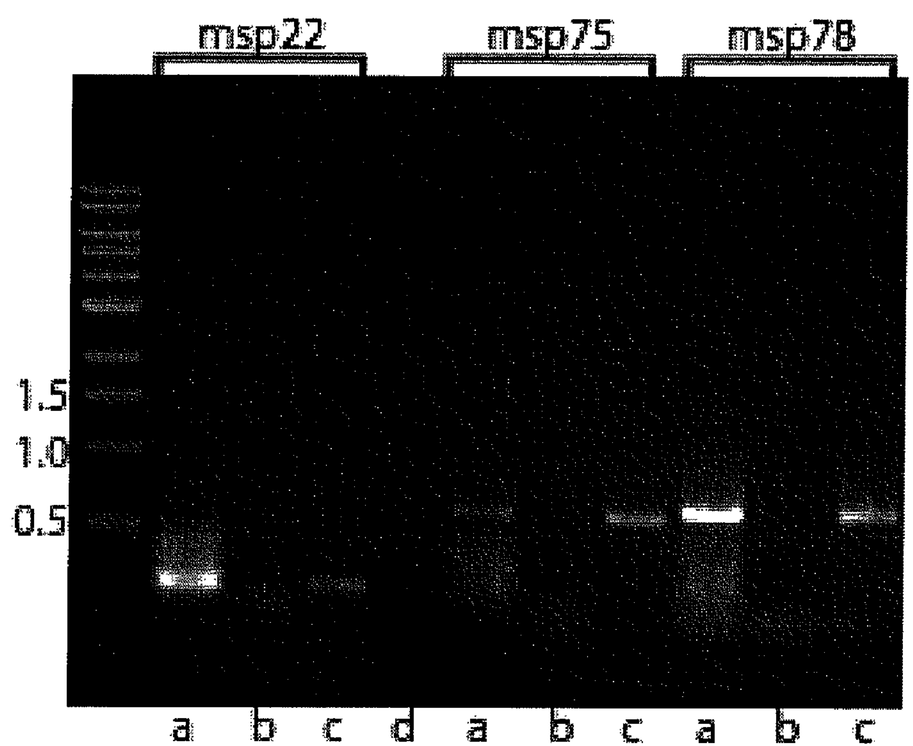
FIG. 3 provides a photographic representation of ethidium bromide stained agarose gels showing results of RT-PCR with RNA from *M. catarrhalis*. Primers used in the reactions corresponded to genes msp22, msp 75 and msp78 as noted at the top of the gel. Lanes a, purified RNA amplified with reverse transcriptase; lanes b, purified RNA amplified with TaqI polymerase to exclude DNA contamination; lanes c, purified DNA amplified with TaqI polymerase; lane d, distilled water with reverse transcriptase as a negative control. Molecular size markers are noted in kilobases on the left.

Transcription of genes during in vitro growth. To determine whether the genes that encode Msp 22, Msp75 and Msp78 are transcribed, RT-PCR was performed using RNA isolated from *M. catarrhalis* strain O35E grown in broth. FIG. 3 (lanes a) shows that all 3 genes are transcribed during growth in vitro. Control assays confirmed that the purified RNA was free of contaminating DNA (lanes b).

EXAMPLE 6

Figure 4:
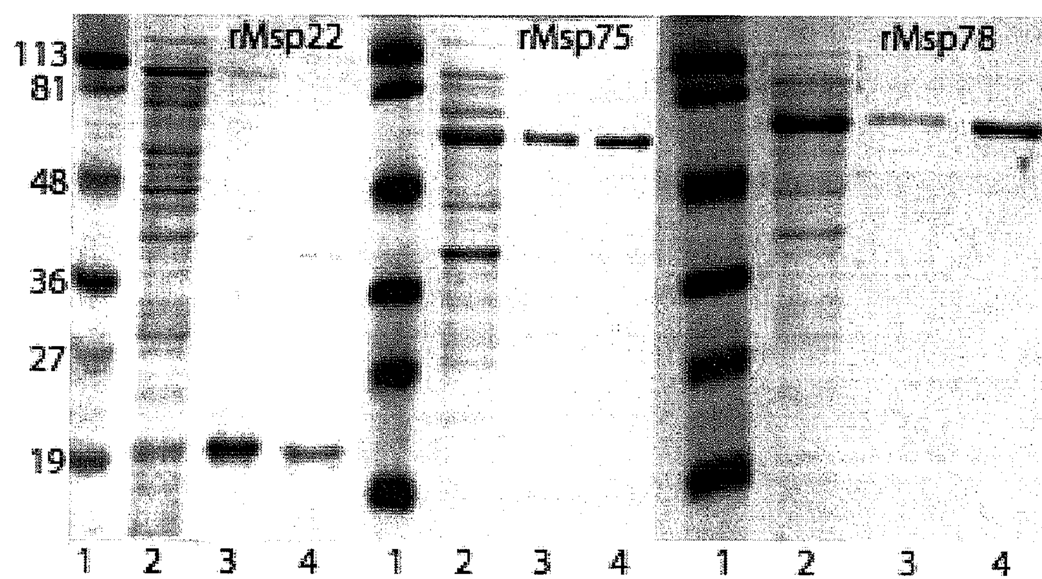
FIG. 4 provides a photographic representation of Coomassie blue stained SDS-PAGE gel showing purification of rMsp22 (22 kDa), rMsp75 (75 kDa), and rMsp78 (78 kDa) proteins. Lane 1, standard; 2, unbound supernatant after binding protein to cobalt resin; 3, cobalt resin after elution of protein with imidazole showing some protein that remains bound to the resin and does not elute; 4, eluted protein after diafiltration into Buffer Z1. Molecular mass standards are noted on the left in kilodaltons (kDa).

Characterization of purified recombinant proteins. Recombinant proteins described for use in the method of the invention were expressed in *E. coli* BL21 (DE3). All three recombinant proteins were purified initially under denaturing conditions. The 6×-His tag was used to bind the protein to cobalt affinity resin, allowing for purification. Denatured protein precipitated at low concentrations when 8M urea was removed. When the proteins were refolded by diafiltrating against buffer Z1, concentrations of approximately 1 mg/ml were obtained. The solubility at a higher protein concentration suggests that the proteins were in a refolded state. The results of a typical purification are shown in FIG. 4. Single bands for each of the proteins were seen when the purified proteins were subjected to sodium dodecyl sulfate polyacrylamide gel electrophoresis (SDS-PAGE).

EXAMPLE 7

Human antibody responses. To determine whether proteins Msp22, Msp75, and Msp78 were expressed by *M. catarrhalis* in the human respiratory tract, the three purified recombinant proteins were assayed with 31 serum and sputum pairs from 31 patients who acquired and cleared *M. catarrhalis* and were found to have developed new serum IgG and sputum IgA antibodies following infection by ELISA and flow cytometry with whole bacteria. These 31 pairs were examined for antibody production to each of the recombinant proteins. Paired pre-acquisition and post-clearance samples were always tested in the same assay.

To determine the cutoff value for a significant percentage change between pre-acquisition and post-clearance in serum IgG and sputum IgA levels, 10 control pairs were examined using a known method (Murphy, T. F. et al. 2003. Infect Immun 71:1288-1294; Adlowitz, D. G., et al. 2005. Infect Immun 73:6601-6607; Adlowitz, et al. 2006. FEMS Immunol Med Microbiol 46:139-146). Briefly, control samples 2 months apart (the same time interval for the experimental samples) from patients who had negative sputum cultures for *M. catarrhalis* were identified. The samples were subjected to ELISA with the purified proteins Msp22, Msp75 and Msp78. Samples that generated $OD_{450}$ values of less than 0.1 were considered not to represent a significant level of antibody, so values of zero were assigned. The % change in $OD_{450}$ values between the paired control samples was calculated. Table 3 shows the means, standard deviations, and upper limits of the 99% confidence intervals (cutoff values) calculated from control samples for the 3 proteins. The cutoff values for a significant change were higher for sputum IgA compared to serum IgG. For Table 3, SD=standard deviation; [a] 99% CI=upper limit of the 99% confidence interval for the control samples. Any percent change in OD450 of greater than the upper limit of the 99% confidence interval between pre-acquisition and post-clearance for that protein was regarded as a significant change; [b]OD values lower than 0.1 were considered not to represent a significant level of antibody, and values of zero were assigned.

TABLE 3

| | rMsp22 | | rMsp75 | | rMsp78 | |
|---|---|---|---|---|---|---|
| | mean ± SD | 99% CI[a] | mean ± SD | 99% CI | mean ± SD | 99% CI |
| Serum IgG | −2.5% ± 8.1% | 18.4% | −40.0% ± 25.5% | 25.8% | −21.1% ± 15.1% | 17.7% |
| Sputum IgA | 61.9% ± 137.4% | 416.4% | 0% ± 0%[b] | 0% | −10.3% ± 31.0% | 69.6% |

Figure 5:
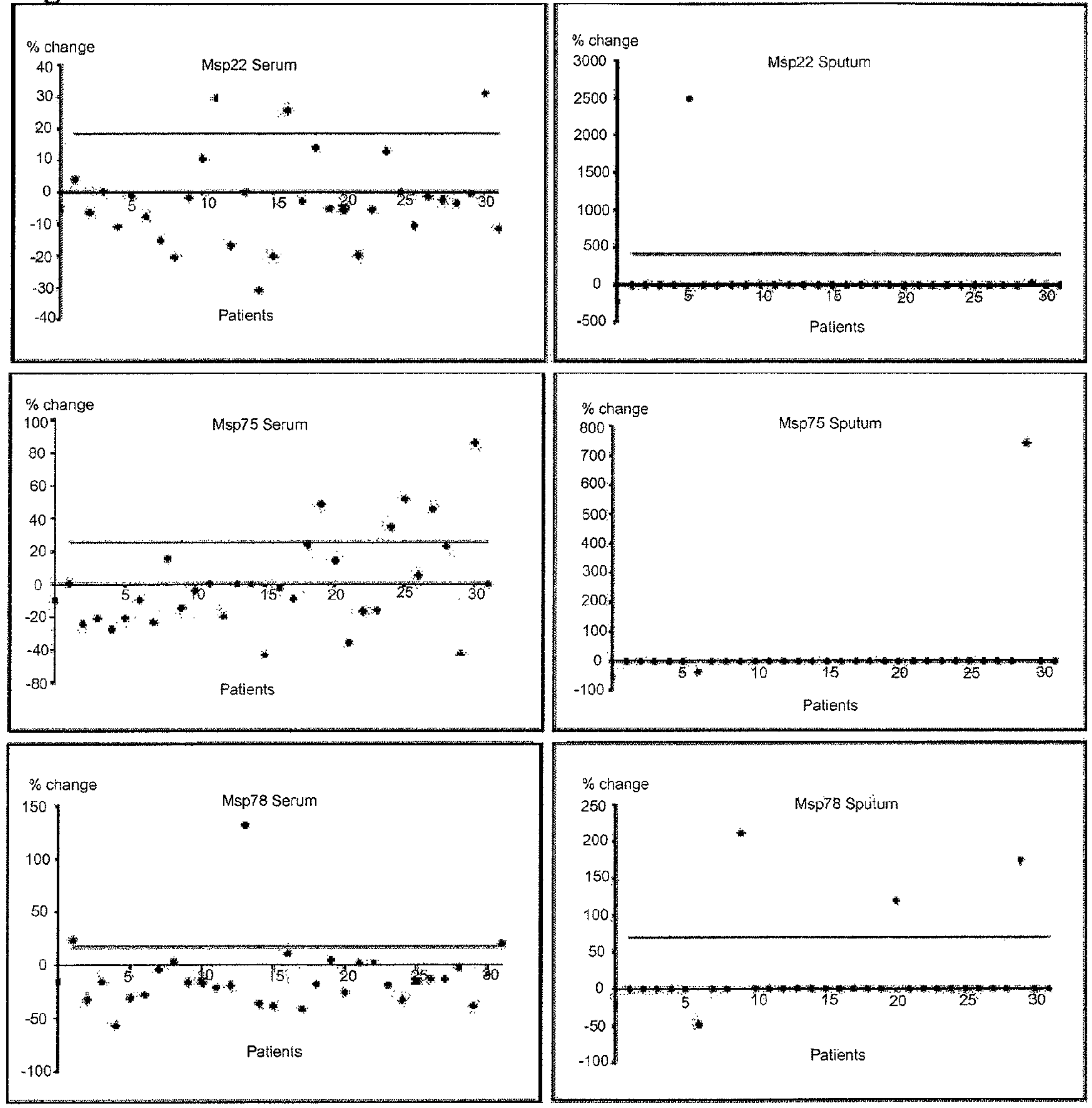
FIG. 5 provides a graphical representation of results of enzyme-linked Immunosorbent assays (ELISAs) measuring serum IgG and sputum IgA to recombinant proteins rMsp22, rMsp75, and rMsp78 in serum and sputum supernatants of adults with COPD who acquired and cleared *M. catarrhalis*. Patient tested is shown on the x-axis. Percent change from pre-acquisition to post-clearance is shown on the y-axis. Cut-off values were determined by averaging the difference between 10 control pairs of sera or sputum from patients who had never been colonized with *M. catarrhalis*. Samples that generated $OD_{450}$ values of less than 0.1 were considered not to represent a significant level of antibody, and values of zero were assigned.
Figure 6:
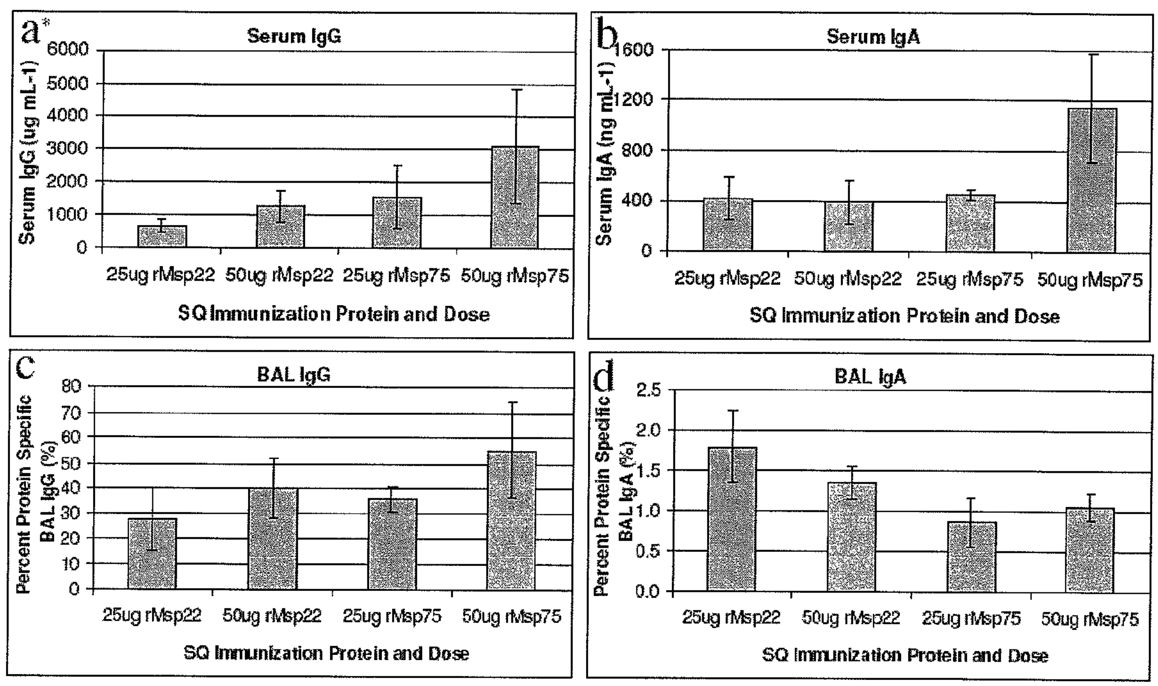
FIG. 6 provides a graphical representation of analysis of IgG and IgA levels to their respective recombinant proteins in serum and BAL fluids as determined by quantitative ELISA for subcutaneously immunized animals. For BAL fluids, values represent amount of protein-specific IgG or IgA divided by the total amount of IgG or IgA present in the BAL fluid. Serum and BAL fluids from negative control animals yielded undetectable levels. Error bars represent standard error of the mean (n=5).
Figure 7:
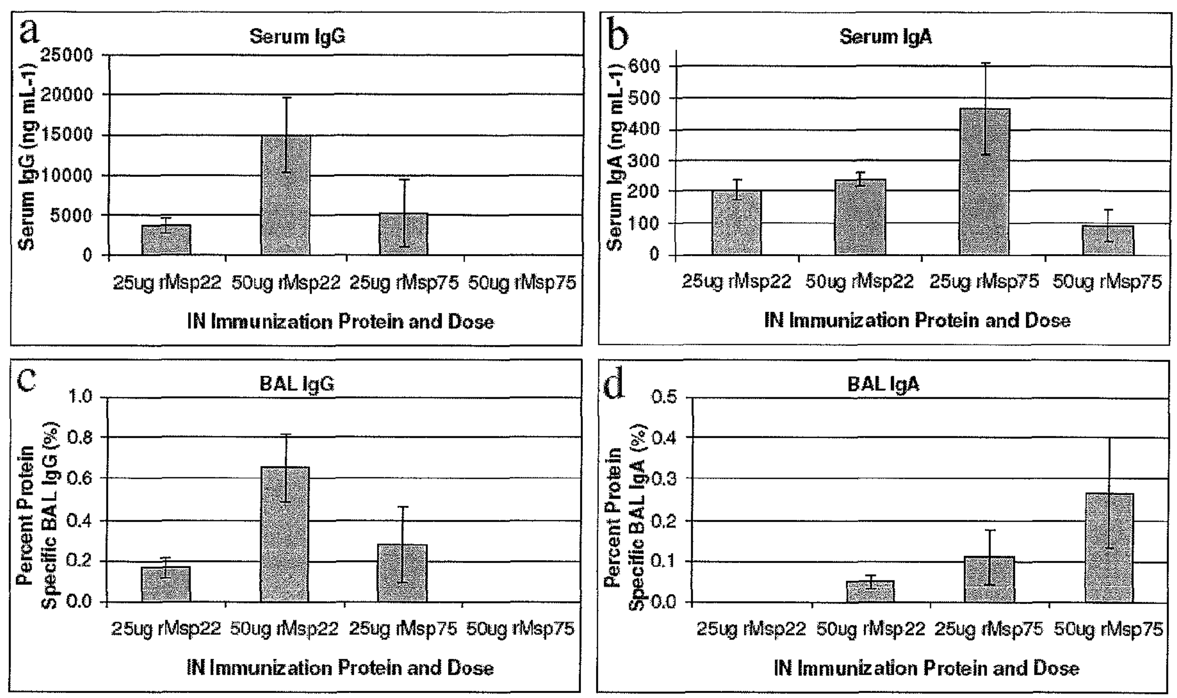
FIG. 7 provides a graphical representation of analysis of IgG and IgA levels to their respective recombinant proteins in serum and BAL fluids as determined by quantitative ELISA for intranasally immunized animals. For BAL fluids, values represent amount of protein-specific IgG or IgA divided by the total amount of IgG or IgA present in the BAL fluid. Serum and BAL fluids from negative control animals yielded undetectable levels. Error bars represent standard error of the mean (n=5).

Results from the ELISA analyses of 31 pairs of serum and sputum with all 3 recombinant proteins are shown in FIG. 5. A significant increase of IgG antibodies to individual proteins was seen in 3% to 16% of patients for each of the proteins. Similarly, 3% to 10% of patients generated a new IgA response to the individual proteins. Overall, 47% of patients generated an antibody response to at least one of the three proteins. These results indicate that Msp22, Msp75, and Msp78 are expressed by *M. catarrhalis* in the human respiratory tract and are targets of the human systemic and mucosal immune systems in a proportion of adults with COPD.

EXAMPLE 8

This Example demonstrates the bactericidal activity of antiserum to Proteins 28, 99 and 238.

To obtain the data presented in this Example, Rabbit antisera to proteins 28, 99 and 238 were raised using standard methods. Briefly, rabbits were immunized subcutaneously separately with each protein on days 1, 28, 42, 60 and 78. Blood was obtained on day 102.

To determine whether antibodies to proteins 28, 99 and 238 have bactericidal activity for *M. catarrhalis*, bactericidal assays were performed. Bactericidal assays with *M. catarrhalis* are problematic because of the relative resistance of the bacterium to serum bactericidal activity. The mechanism of this resistance involves the surface protein UspA2 which is expressed by all strains of *M. catarrhalis*. UspA2 binds vitronectin which interferes with complement fixation, in particular the formation of the membrane attack complex by C5-C9. To circumvent this variable, bactericidal assays were performed with a mutant of *M. catarrhalis* strain O35E (strain O35E.2) in which the uspa2 gene was knocked out and thus the mutant expresses no UspA2 on its surface. This mutant is substantially more sensitive to serum killing than the wild type strain.

The complement source for the bactericidal assays was prepared from normal human serum which was adsorbed with protein G to remove much of the IgG antibody. The adsorbed serum was then adsorbed further with glutaraldehyde-fixed bacterial cells of the UspA2 mutant. In negative control assays, this adsorbed serum did not kill the UspA2 mutant. In positive control assays, this adsorbed serum supported complement-mediated killing with heat inactivated serum, indicating that active complement was present in the complement source.

To perform bactericidal assays, logarithmic phase cells of strain O35E.2 were incubated with dilutions of rabbit antiserum and the complement source (20% of the volume of the assay reaction) described above. The number of viable bacteria was determined by colony counts at time 0 and after 30 minutes incubation at 37° C. The % kill was calculated from the colony counts.

Results of assays with rabbit antiserum to proteins 28, 99 and 238 are shown in Table 4. The lowest concentration of serum that produced maximum killing is shown.

TABLE 4

| Antiserum | Concentration of serum | % kill after 30 minutes |
|---|---|---|
| Anti-28 | 10% | 93% |
| Anti-99 | 2.5% | 98% |
| Anti-238 | 20% | 56% |

Negative controls included rabbit serum without complement (no kill) and complement without rabbit serum (no kill). These assays have been performed three times independently, each on separate days. The results are highly reproducible. Thus, this Example demonstrates that Protein 28, Protein 99, and Protein 238 are capable of stimulating an immune response comprising anti-28, anti-99 and anti-238 antibodies, and that the stimulated antibodies are effective in killing *M. catarrhalis*.

EXAMPLE 9

This Example provides a description of the materials and methods used to obtain the data presented in Examples 10-12. (Expression and purification of recombinant proteins was performed essentially as set forth in Example 1.) Examples 10-12 demonstrate analysis of Msp22 and Msp75 in a mouse pulmonary clearance model using subcutaneous and intranasal administrations. Quantitative ELISAs were also performed on sera and bronchoalveolar lavage (BAL) fluids from the immunized mice to characterize systemic and mucosal antibody responses. Analysis of sera by flow cytometry and whole cell ELISA detected antibodies that bound to the bacterial surface of multiple strains of *M. catarrhalis*. Mice immunized with the recombinant proteins showed enhanced clearance of *M. catarrhalis* as compared to control mice in a mouse pulmonary clearance model. These Examples indicate that newly identified Msp22 and Msp75 proteins are conserved surface proteins that induce potentially prophylactic immune responses.

Bacterial strains and culture conditions. *M. catarrhalis* strain 43617 was obtained from the American Type Culture Collection (Rockville, Md.). Strain O35E was provided by Eric Hansen. Middle ear fluid isolates 2951, 7169, and 8184 were provided by Dr. Howard Faden. Strains 6P29B1, 7P94B1, and 102P19B1 were sputum isolates obtained from adults in our COPD study clinic (28, 31). Chemically competent *Escherichia coli* strains TOP 10 and BL21(DE3) were obtained from Invitrogen.

*M. catarrhalis* strains were grown on brain heart infusion (BHI) plates at 37° C. with 5% $CO_2$ or in BHI broth with shaking at 37° C. *E. coli* strains were grown on Luria-Bertani (LB) plates, LB broth, or in terrific broth (TB) at 37° C. supplemented with the appropriate antibiotics (MoBio Laboratories, Carlsbad, Calif.).

Systemic immunizations. Groups of five Balb/c mice each were immunized subcutaneously (SQ) with 25 μg or 50 μg of either Msp22 or Msp75 emulsified in incomplete Freund's adjuvant (IFA). Additional groups of five mice each were immunized with either adjuvant alone (negative control) or formalin killed *M. catarrhalis* O35E emulsified in IFA (positive control). Injections were repeated at 14 and 28 days after the initial immunization. Mice were challenged as described below on day 35.

Mucosal immunizations. Groups of five Balb/c mice were immunized intranasally (IN) with 25 μg or 50 μg of either Msp22 or Msp75. Cholera toxin (CT) (1 μg) was included as a mucosal adjuvant. Additional groups of five mice each were immunized with either 1 μg CT (negative control) or formalin killed *M. catarrhalis* O35E with 1 μg CT (positive control). IN immunization were performed by having awake animals sniff liquid from a pipette tip placed at the nostril. A volume of 5 μl per nostril at a time was administered. Immunizations were repeated at days 10 and 20 after the initial immunization. Mice were challenged as described below on day 28.

Enzyme-linked immunosorbent assays. ELISA was employed to quantitate the antibody responses following both subcutaneous and mucosal immunizations with the recombinant proteins. The optimal protein concentrations (2 to 10 μg) and starting dilutions were determined in preliminary assays. To assay antibody to recombinant protein, wells of Immunolon 4 plates (Thermo Labsystems, Franklin, Mass.) were coated with purified protein by overnight incubation at room temperature. Plates were washed 4 times with PBST (phosphate buffered saline, 0.5% Tween 20) and then blocked using 2% nonfat dry milk in PBS (MPBS) for 1 h at room temperature. After washing, dilutions of serum or BAL fluid in MPBS plus 0.02% sodium azide were added to wells and incubated at room temperature overnight. Wells were washed 4 times with PBST and HRP-conjugated anti-mouse IgG (1:3000) or anti-mouse IgA (1:2000) diluted in MPBS was added. After incubating at room temperature for 4-6 h, wells were washed and developing reagent was added to the wells and incubated for 15 min in the dark. Color development was stopped using $4NH_2SO_4$. Absorbance at 490 nm was read using a BioRad microplate reader.

To calculate antibody concentrations, a standard curve was constructed on each microtiter plate and run simultaneously with experimental samples. Wells were coated with 1 μg/ml of anti-mouse IgG or anti-mouse IgA. Standardized amounts of IgG or IgA were incubated in coated wells overnight. Wells were washed 4 times with PBST and HRP-conjugated anti-mouse IgG (1:3000) or anti-mouse IgA (1:2000) diluted in MPBS was added, followed by color developer as described above. Concentrations of IgG and IgA were determined based on standard curves using a four-parameter logistic method of calculation (Microplate Manager III, BioRad).

BAL IgG and IgA levels were expressed as a percentage of protein-specific antibody level as compared to total IgG or IgA present to correct for volume differences actually obtained in the lavage fluid. To determine this, each sample was examined by ELISA twice, once to assay the amount antibody that recognized the recombinant protein as described above, and a second time to determine the total amount of IgG or IgA present in the sample. To measure total IgG and IgA, wells were coated with 1 μg/ml anti-mouse IgG or 1 μg/ml anti-mouse IgA instead of recombinant protein. Total immunoglobulin concentrations were calculated from standard curves performed as described in the previous paragraph. To calculate the protein specific antibody level, the concentration of antibody to the recombinant protein is divided by the total antibody concentration individually for IgG and IgA.

Flow cytometry. Sera from the subcutaneously immunized mice were subjected to flow cytometry to determine if the antibodies produced against the recombinant proteins bound to surface exposed epitopes. Nine strains of *M. catarrhalis* (O35E, O35E.2, 43617, 2951, 7769, 8184, 6P29B1, 7P9B1, and 102P19B1) were grown to mid-logarithmic phase in broth ($OD_{600}$≈0.2). An aliquot of 200 μl was harvested by centrifugation at 16,000×g for 5 min and resuspended in 200 μl of a 1:25, 1:50, or 1:100 dilution of mouse serum. One sample was resuspended in PBS in the absence of serum as a negative control. The sera were incubated with the bacteria for 1 h at 37° C. Bacteria were again centrifuged and resuspended in 200 μl of 50 μg/ml fluorescein isothiocyanate (FITC) labeled goat-anti-mouse IgG (KPL, Gaithersburg, Md.). Samples were incubated at 37° C. for 30 min then added to 1.8 ml PBS. The fluorescence intensity was read on a FACScan flow cytometer (Becton Dickinson). A total of 20,000 cells were counted per sample by gating on intact cells based on forward and side-scatter characteristics (CELLQuest ver 3.3, Becton Dickinson).

Pulmonary challenge model. On day 35 (SQ) or day 28 (IN), mice were challenged using an inhalational system (18). All immunizations and murine procedures were performed in compliance with Veterans Affairs Western New York Heathcare System IACUC guidelines. An overnight culture of *M. catarrhalis O*35E was diluted in phosphate buffer saline with gelatin, calcium, and magnesium (PBSG; 137 mM NaCl, 2.7 mM KCl, 4.3 mM $NaHPO_4$, 1.4 mM $KH_2PO_4$, 0.12 5 mM $CaCl_2$, 0.5 mM $MgCl_2$, 0.1% gelatin, pH 7.3) to an $OD_{600}$≈0.3-0.4 ($1\times10^8$ CFU) and 10 ml of the diluted culture was placed in the nebulizer of an Inhalational Exposure System model 099C A4212 (Glas-Col, Terre Haute, Ind.). An additional aliquot of culture was diluted to $10^{-5}$ and 20 μl was plated to determine the starting amount of bacteria. The equipment settings were as follows: 10 min preheat, 40 min nebulization, 30 min cloud decay, 10 min decontamination, vacuum flowmeter at 60 cubic feet/hour, compressed air flowmeter at 10 cubic feet/hour.

Three hours post-challenge, the mice were anesthetized by inhalation of isoflurane and bled by retro-orbital puncture. Blood from each mouse was allowed to clot on ice. Serum was then isolated, heat inactivated at 56° C. for 30 min, aliquoted, and frozen at −20° C. Mice were subjected to additional isoflurane to ensure death.

Bronchoalveolar lavage (BAL) fluid was then collected. To obtain BAL samples, a blunt 22 gauge needle was inserted into the trachea. A total of 2 mL PBSG was administered in 3 doses and the lavage fluid was collected by syringe aspiration. The BAL fluid was filter sterilized and stored at −20° C.

Lungs were harvested and placed in 5 ml PBSG. They were homogenized on ice using a tissue homogenizer. Following homogenization, 250 μl of each lung homgenate was plated and incubated at 35° C. with 5% $CO_2$ overnight. Colonies were counted the following day to determine the concentration of bacteria in the lungs. Statistical significance was determined by performing two-tailed t-tests. A p value of $\leqq 0.05$ was considered significant.

EXAMPLE 10

Immunogenicity of recombinant proteins. ELISAs were employed to assess antibody responses to the recombinant proteins (FIGS. 6*a*-*d* and 7*a*-*d*). To correct for volume differences actually obtained in the lavage fluid, BAL IgG and IgA levels were expressed as a percentage of protein-specific antibody level by dividing the protein specific antibody concentration by total antibody concentration for both IgG and IgA.

For all groups, immunization with Msp22 and Msp75 induced an antibody response with measurable levels of IgG and IgA antibodies in the serum and BAL fluids as compared to the adjuvant control mice, which had undetectable levels, indicating that both proteins were immunogenic. Subcutaneous immunizations induced approximately one log greater serum IgG level as compared to IN immunization, as expected. A trend towards dose dependence was seen in the serum IgG levels for both proteins when immunized subcutaneously. Both intranasal and subcutaneous routes of immunizations generated BAL IgG and BAL IgA antibodies. Levels of antigen specific IgG in the BAL samples were high in the SQ immunized animals with the same trend of dose dependence observed as with serum IgG. Protein specific IgA antibodies in the BAL fluids were all less that 2% of the total IgA present for both the SQ and IN immunized mice, a lower proportion than expected. We conclude that both Msp22 and Msp75 were immunogenic in mice when administered by systemic and mucosal routes.

EXAMPLE 11

Figure 8:
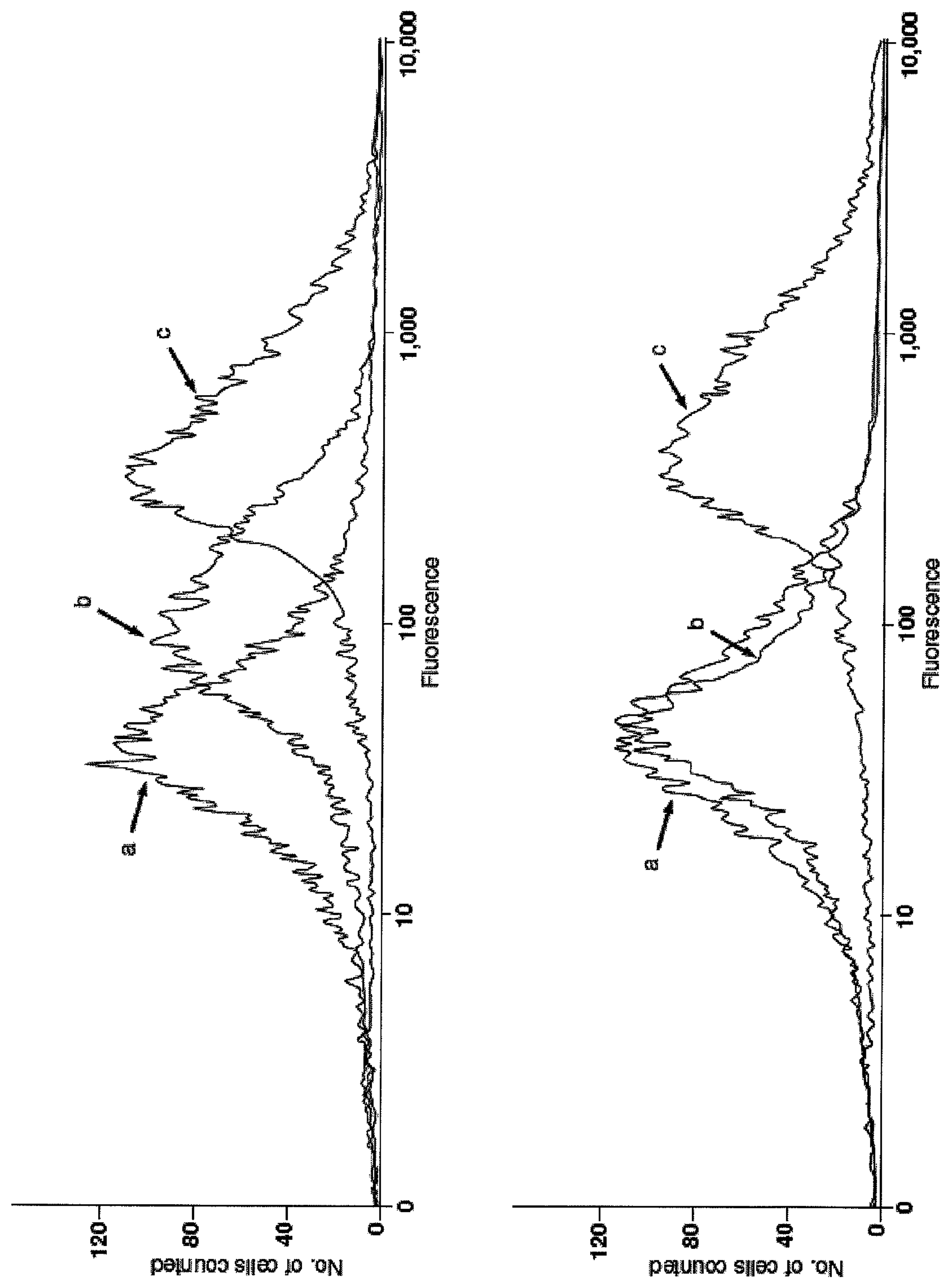
FIG. 8 provides a graphical representation of analysis of typical results of flow cytometry with *M. catarrhalis* strain O35E to measure serum IgG following immunization with recombinant proteins. Serum samples are at 1:25 (top) and 1:50 (bottom). Line a) adjuvant immunized mouse sera (negative control); Line b) 25 μg Msp22 SQ immunized mouse sera; Line c) formalin-killed *M. catarrhalis* O35E immunized mouse sera (positive control).

Analysis of antibodies to surface epitopes by flow cytometry. Flow cytometry was employed to determine if the antisera raised to Msp22 and Msp75 in mice contained antibodies directed at surface exposed epitopes. FIG. 8 shows the results with strain O35E examined using antisera to Msp22. The level of fluorescence with antisera to Msp22 was greater than that observed with the negative control (serum from mice immunized with adjuvant alone) as indicated by a shift to the right on the x-axis.

To determine the level of fluorescence that was statistically different from the negative control, *M. catarrhalis* O35E was subjected to flow cytometry with negative control sera and each protein antisera in triplicate. The mean and median fluorescence levels on the x-axis for each antiserum were determined at a 1:25 dilution. The calculations below were performed separately using the median fluorescence values and the mean fluorescence values. Both yielded similar results so the median values and calculations are shown.

Figure 9:
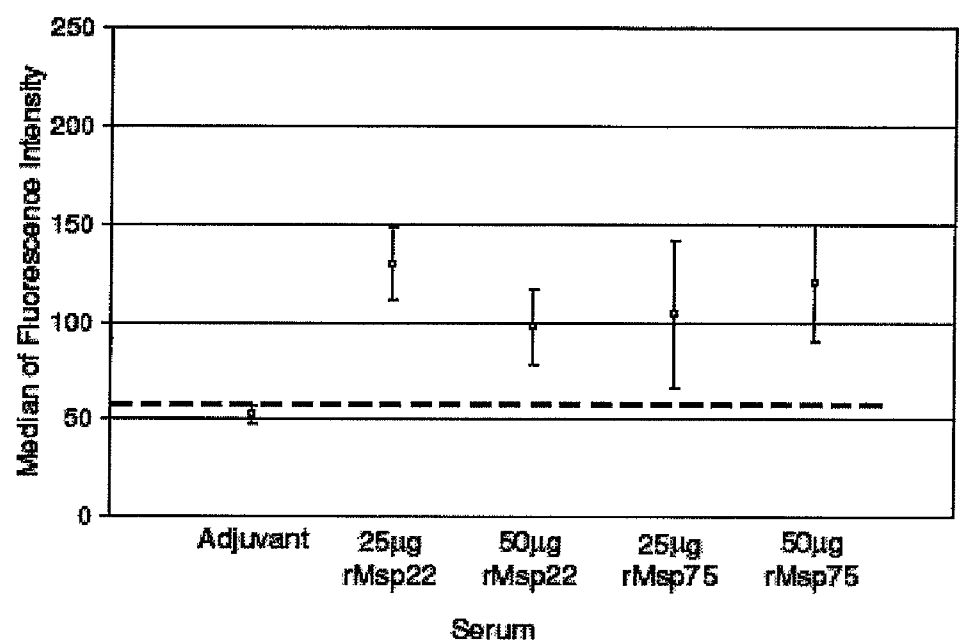
FIG. 9 provides a graphical representation of results of flow cytometry using strain O35E. Mouse sera examined at a 1:25 dilution are on the x-axis. Median fluorescence intensity (arbitrary units) are on the y-axis. The dashed line represents the upper limit of the 95% confidence interval (CI) for the adjuvant immunized negative control (57.35). Error bars=95% CI for the triplicate runs. All of the SQ sera tested had the lower limit of their 95% confidence interval exceed the cutoff value of 57.35 and therefore were considered to be significant.

The median of the value for the negative control mice was 52.22±2.62 (median±standard deviation) fluorescence units. The upper level of the 95% confidence interval was represented by a median fluorescence of 57.35. Therefore, samples with the lower level of their 95% confidence interval of the triplicate assays that were greater than the cutoff median fluorescence value of 57.35 were considered to be significant. The sera generated by systemic immunization of groups of mice with each of the proteins individually yielded values that were above the median cutoff indicating that the shift was due to specific binding of antibodies to the bacterial surface (FIG. 9). In contrast, IgG in sera generated by IN immunization of groups of mice with Msp22 and Msp75 individually did not show an increase in fluorescence as compared to the negative control serum. These experiments indicate that systemic immunization with recombinant proteins Msp22 and Msp75 individually each induced serum IgG antibodies that bound to surface exposed epitopes in strain O35E.

To assess the extent that antibodies were directed towards epitopes on the surface of other strains of *M. catarrhalis*, sera from animals immunized subcutaneously with the recombinant proteins were examined by flow cytometry with 8 additional strains. Sera from animals immunized with Msp22 and Msp75 showed an increase in fluorescence similar to that seen with O35E for all 8 strains examined, as compared to the negative control sera at the same dilution. We conclude that antibodies induced by immunization individually with both Msp22 and Msp75 recognized epitopes that are present on the surface of multiple strains of *M. catarrhalis*.

EXAMPLE 12

Enhancement of pulmonary clearance. The mouse pulmonary clearance model is simple, reproducible, and allows for examination of a functional immune response. In this model, mice to which test antigens are administered are subsequently challenged with bacteria. After a period of 3 hours, lungs are harvested and clearance of bacteria is determined.

Figure 10:
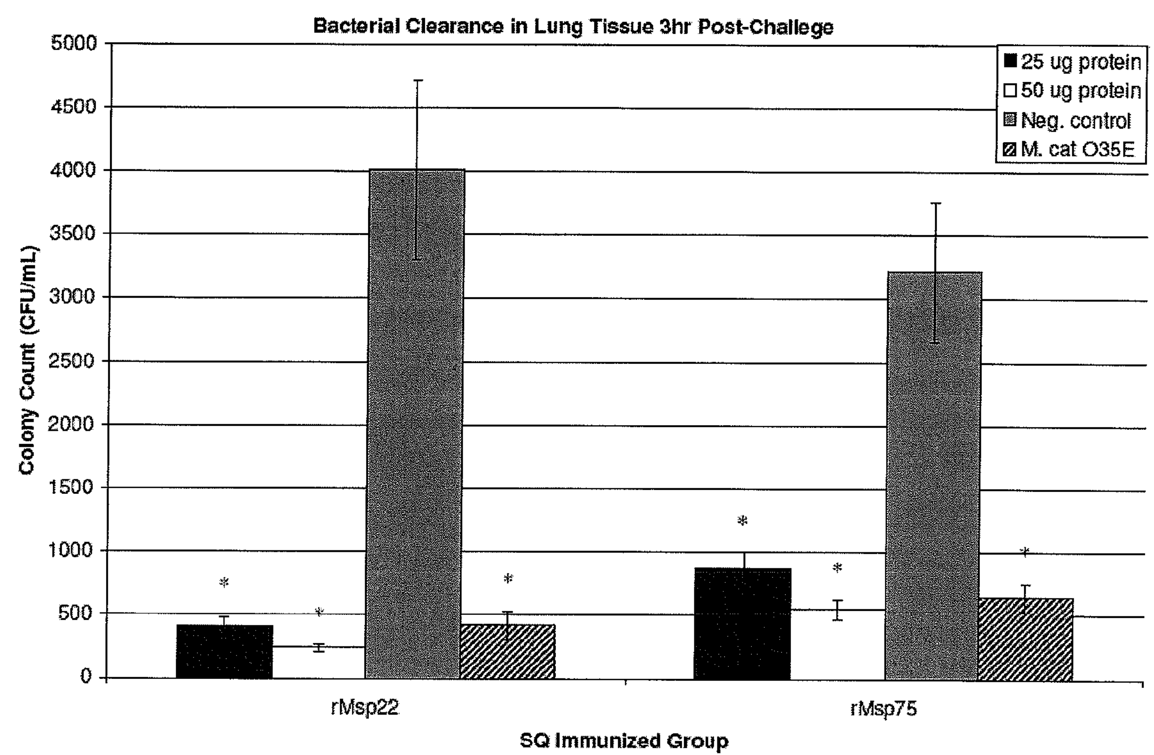
FIG. 10 provides a graphical representation of homogenized lung colony counts 3 hours post-*M. catarrhalis* aerosol challenge following SQ immunization. Error bars represent the standard error of the mean (n=5).* p-value<0.05 as compared to the negative control.
Figure 11:
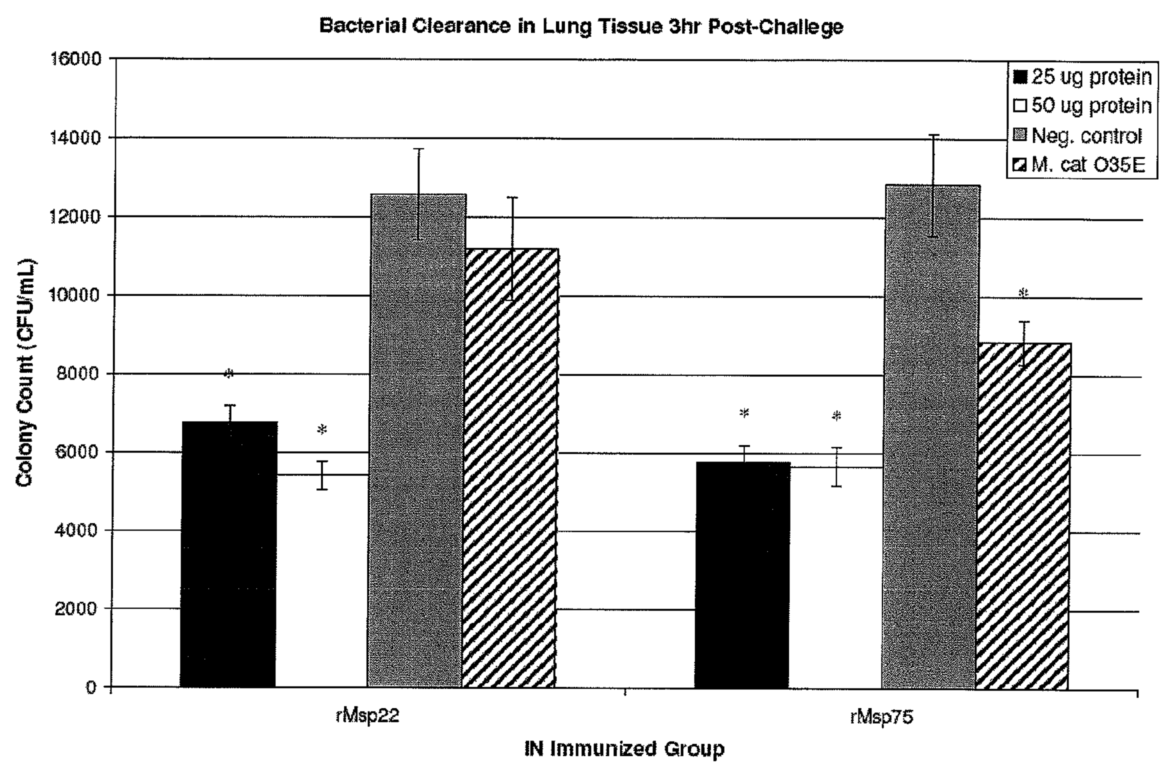
FIG. 11 provides a graphical representation of homogenized lung colony counts 3 hours post-*M. catarrhalis* aerosol challenge following IN immunization. Error bars represent the standard error of the mean (n=5).* p-value<0.05 as compared to the negative control.

To determine whether immunization with Msp22 and/or Msp75 would enhance pulmonary clearance of *M. catarrhalis*, groups of mice were immunized three times each either subcutaneously or intranasally. Positive control mice were immunized with formalin-killed *M. catarrhalis O*35E, as immunization with whole organism is known to induce enhanced clearance in this model. Mice were challenged with live bacteria one week after their last boost. Following challenge with strain O35E, the quantity of bacteria recovered from the lungs of mice that received the recombinant proteins were significantly lower than bacteria recovered from the control mice immunized with adjuvant alone (FIGS. 10 and 11). Two-tailed t-tests were performed to determine the statistical significances of the clearance results.

A significant difference was seen between Msp22 and sham (adjuvant) immunized mice for both the 25 μg and 50 μg doses via the SQ route of vaccination. A significant difference was also seen between sham (adjuvant) immunized and Msp75 immunized mice in for both the 25 μg and 50 μg doses.

As with the SQ route, mice immunized intranasally with Msp22 showed enhanced clearance with both the 25 μg and 50 μg doses. A significant difference was also seen between rMsp75 and sham (adjuvant) immunized mice for both the 25 μg and 50 μg doses via the IN route of vaccination. Collectively, these data show between one half to one log difference between the sham and recombinant protein immunized groups, indicating that immunization with rMsp22 and rMsp75 induced enhanced pulmonary clearance in a mouse model.

Thus, Examples 9-12 demonstrate that both Msp22 and Msp75 are immunogenic in mice when immunized via subcutaneous and/or intranasal routes of administration. Msp22 and Msp75 were confirmed to be in the outer membrane using flow cytometry. The proteins had surface exposed epitopes that are present in multiple strains of *M. catarrhalis*. The in vivo pulmonary clearance analysis demonstrates that both Msp22 and Msp75 enhanced pulmonary clearance.

The preceding Examples are meant to illustrate specific embodiments but not limit the invention.

We claim:

1. A method for stimulating in an individual an immune response against *Moraxella catarrhalis* comprising administering to the individual a composition comprising at least one isolated *Moraxella catarrhalis* protein, wherein the at least one isolated *Moraxella catarrhalis* protein comprises the amino acid sequence of SEQ ID NO:1 or the amino acid sequence of SEQ ID NO:3, and wherein the administering of the at least one isolated *Moraxella catarrhalis* protein results in a stimulated immune response against *Moraxella catarrhalis* in the individual.

2. The method of claim 1, wherein the composition further comprises an isolated protein selected from the group of proteins consisting of a protein comprising the amino acid sequence of SEQ ID NO:5, a protein comprising the amino acid sequence of SEQ ID NO:7, a protein comprising the amino acid sequence of SEQ ID NO:9, a protein comprising the amino acid sequence of SEQ ID NO:11, and combinations thereof.

3. The method of claim 1, wherein the composition further comprises an adjuvant.

4. The method of claim 1, wherein the composition further comprises a pharmaceutically acceptable carrier.

5. The method of claim 1, wherein the composition is administered to the individual by a route selected from subcutaneous, intramuscular, intravenous, intradermal, intranasal, oral and inhalation administrations.

6. The method of claim 5, wherein the composition is administered to the individual by a route selected from subcutaneous administration and inhalation administration.

7. The method of claim 1, wherein the stimulated immune response in the individual comprises generation of antibodies against *Moraxella catarrhalis*.

8. The method of claim 7, wherein the generation of antibodies comprises generation of IgG and/or IgA antibodies.

9. The method of claim 1, wherein the stimulated immune response is associated with an enhanced rate of *Moraxella catarrhalis* bacterial clearance from the lungs of an individual to whom the composition is administered.

10. The method of claim 1, wherein the composition is administered to the individual as several doses over a period of time.

11. The method of claim 1, wherein the stimulated immune response is prophylactic against *Moraxella catarrhalis* infection in the individual.

12. The method of claim 1, further comprising administering an antibiotic agent to the individual.

* * * * *

UNITED STATES PATENT AND TRADEMARK OFFICE

CERTIFICATE OF CORRECTION

PATENT NO. : 7,811,589 B2
APPLICATION NO. : 12/345430
DATED : October 12, 2010
INVENTOR(S) : Timothy Murphy et al.

It is certified that error appears in the above-identified patent and that said Letters Patent is hereby corrected as shown below:

Col. 1, lines 9-10 should read

"This invention was made with Government under Grant No. AI028304 awarded by the National Institutes of Health. The Government has certain rights in the invention."

Signed and Sealed this
Twenty-ninth Day of January, 2013

David J. Kappos
*Director of the United States Patent and Trademark Office*

SEQUENCE LISTING

```
<160> NUMBER OF SEQ ID NOS: 24

<210> SEQ ID NO 1
<211> LENGTH: 152
<212> TYPE: PRT
<213> ORGANISM: Moraxella catarrhalis

<400> SEQUENCE: 1

Met Phe His Lys Ile Thr Leu Ala Ala Ala Cys Phe Met Thr Val Ile
1               5                   10                  15

Leu Ala Gly Cys Asn Ser Ser Gly Thr Ala Thr Ala Asn Asn Pro Gln
            20                  25                  30

Val Glu Asp Arg Ala Lys Leu Met Lys Asp Trp Arg His Ala Asn Glu
        35                  40                  45

Gly Met Lys Ala Met Ile Glu Asp Pro Ser Arg Phe Asp Ala Ile Thr
    50                  55                  60

Phe Lys Glu Arg Ala Asp Phe Ile Ala Asp Thr Asn Ala Thr Met Trp
65                  70                  75                  80

Val His Phe Glu Gly Glu Met Ala Gln Gly Gly His Ala Lys Asp Glu
                85                  90                  95

Ile Trp Thr Asp Pro Glu Gly Phe Lys Thr Lys Ile Glu Ala Phe Thr
            100                 105                 110

Ser Ser Ile Asn Ala Leu Ala Leu Ala Ala Ser Glu Ala Ala Ser Ala
        115                 120                 125

Ala Asp Val Glu Ala Ser Tyr Gly Glu Met Ala Ser Gln Cys Gly Ser
    130                 135                 140

Cys His Lys Ala Tyr Lys Lys Lys
145                 150


<210> SEQ ID NO 2
<211> LENGTH: 458
<212> TYPE: DNA
<213> ORGANISM: Moraxella catarrhalis
```

<400> SEQUENCE: 2

```
atgtttcata aaattacctt agctgctgca tgttttatga ctgttatttt agcaggttgc      60
aacagctcag ggactgccac cgccaataat ccacaggttg aagaccgtgc caaactcatg     120
aaagattggc gtcatgccaa tgagggcatg aaggcaatga ttgaagaccc aagtcgcttt     180
gatgccatca cctttaaaga gcgagctgat tttattgctg ataccaatgc caccatgtgg     240
gtacactttg aaggagaaat ggctcaaggt ggtcatgcta aagatgagat atggacagac     300
cctgaaggct ttaaaaccaa aatcgaagcg tttaccagct caattaatgc acttgcctta     360
gcagcatcag aagctgcctc ggcggctgat gttgaagcaa gctatggtga aatggccagc     420
cagtgtggtt cttgccataa ggcttataag aaaaaata                             458
```

<210> SEQ ID NO 3
<211> LENGTH: 498
<212> TYPE: PRT
<213> ORGANISM: Moraxella catarrhalis

<400> SEQUENCE: 3

```
Met Asn Gln Pro Thr Asn Gln Ser Thr Thr Gln Pro Ser Ser Ile Pro
1               5                   10                  15

Leu Asn Cys Pro Asn Leu Leu Lys Gln Ala Cys Leu Ile Asp Gly Glu
            20                  25                  30

Trp Val Gly Ala Asp Ser Gly Glu Thr Ile Ala Val Thr Asn Pro Phe
        35                  40                  45

Thr Gly Asp Val Leu Gly Thr Ile Pro Ser Leu Ser Lys Gln Thr Val
    50                  55                  60

Leu Asn Ala Val Glu Cys Ala Asp Ala Ala Gln Glu Ser Trp Ala Asn
65                  70                  75                  80

Thr Thr Ala Ser Glu Arg Ala Lys Leu Leu His Ala Trp Ala Asp Leu
                85                  90                  95

Ile Asp Thr His Lys Glu Asp Leu Ala Leu Ile Met Thr Tyr Glu Gln
            100                 105                 110

Gly Lys Pro Ile Thr Glu Ser Gln Gly Glu Ile Asp Tyr Ala Asn Ser
        115                 120                 125

Phe Ile Arg Trp Phe Ala Asp Glu Gly Lys Arg Ile Tyr Gly Asp Val
    130                 135                 140

Ile Pro Ser Thr Asn Gln Ser Leu Arg Tyr Val Val Leu Lys Gln Pro
145                 150                 155                 160

Val Gly Val Cys Ala Ala Ile Thr Pro Trp Asn Phe Pro Ser Ala Met
                165                 170                 175

Ile Ala Arg Lys Ala Ala Pro Ala Leu Ala Ala Gly Cys Thr Met Ile
            180                 185                 190

Ile Lys Pro Ala Val Glu Thr Pro Phe Ser Ala Leu Ala Leu Gly Tyr
        195                 200                 205

Leu Ala Lys Gln Ala Gly Ile Pro Lys Gly Val Leu Gln Ile Val Thr
    210                 215                 220

Gly Lys Ser Ser Val Val Gly Glu Val Leu Thr Lys Asp Pro Arg Ile
225                 230                 235                 240

His Lys Leu Ser Phe Thr Gly Ser Thr Glu Val Gly Arg Val Leu Met
                245                 250                 255

Glu Gln Cys Ala Ser Thr Ile Lys Lys Leu Ser Met Glu Leu Gly Gly
            260                 265                 270

Asn Ala Pro Phe Ile Val Phe Asp Asp Ala Asp Leu Glu Lys Ala Ala
        275                 280                 285
```

-continued

```
Glu Gly Leu Ile Ala Ser Lys Tyr Arg Asn Ala Gly Gln Thr Cys Val
    290                 295                 300

Cys Ala Asn Arg Ile Tyr Val Gln Ser Ser Ile Lys Asp Glu Phe Leu
305                 310                 315                 320

Ala Lys Phe Lys Gln Lys Val Glu Val Leu Lys Val Gly Asn Gly Ala
                325                 330                 335

Asp Glu Ala Thr Asp Ile Gly Pro Leu Ile Asn Gln Gln Ala Leu Lys
            340                 345                 350

Lys Val Gln Ala Leu Leu Asp Asp Ala Leu Asn Lys Gly Ala Thr Leu
        355                 360                 365

Ile Thr Gly Gly Val Pro His Asp Ala Ser Gln Leu Ser Phe Thr Pro
    370                 375                 380

Thr Val Ile Ser Asp Ile Thr Asp Glu Met Asp Leu Ala His Glu Glu
385                 390                 395                 400

Ile Phe Gly Pro Ile Ala Pro Ile Met Thr Phe Glu Asp Glu Lys Glu
                405                 410                 415

Val Ile His Arg Ala Asn Asp Thr Ile Tyr Gly Leu Ala Ala Tyr Phe
            420                 425                 430

Tyr Thr Gln Ser His Ala Arg Ala Trp Arg Val Ser Glu Ala Leu Glu
        435                 440                 445

Tyr Gly Met Val Gly Gln Asn Thr Gly Leu Leu Ser Thr Glu Val Ala
    450                 455                 460

Pro Phe Gly Gly Val Lys Gln Ser Gly Phe Gly Arg Glu Gly Ser Lys
465                 470                 475                 480

Tyr Gly Ile Glu Glu Tyr Ile Thr Thr Lys Tyr Trp Cys Met Asp Ile
                485                 490                 495

Ser Glu


<210> SEQ ID NO 4
<211> LENGTH: 1496
<212> TYPE: DNA
<213> ORGANISM: Moraxella catarrhalis

<400> SEQUENCE: 4

atgaaccaac ctacaaatca atctacgacc caaccctcat cgattccgct taactgcccc     60

aatctgctaa agcaagcctg tttgattgat ggagagtggg ttggtgctga ttctggtgag    120

accatcgcag ttaccaatcc attcacaggc gatgtgcttg gtacgatacc tagcttatca    180

aaacaaaccg ttctaaacgc cgttgagtgt gctgatgctg cccaagaaag ctgggcaaat    240

accaccgcca gtgagcgtgc caaacttttg catgcttggg cggatctgat cgatacacac    300

aaggaagatt tggcactgat catgacctat gagcaaggca agcccatcac agaatcacaa    360

ggtgagattg attatgccaa tagcttcata cgctggtttg cagatgaagg caaacgcatc    420

tatggcgatg ttattccaag taccaatcag tcgctacgct atgtggtact caagcagcca    480

gtcggtgtgt gtgctgcgat tacgccttgg aatttccctt cggcaatgat tgctcgtaaa    540

gctgcacctg cgttagcggc tggctgtacc atgatcatca agccagcggt tgagacgcca    600

ttttcggcat tggcactggg atatttggca aaacaagcag gtattcctaa aggtgtgtta    660

caaattgtta ctggtaaatc ctctgtggtc ggcgaggtac tgaccaaaga tccacgcatt    720

cataagctgt cattcacagg ttctaccgaa gtggggcgag tactgatgga gcaatgtgca    780

agcaccatca aaaagctgtc tatggagctt ggcggtaatg caccttttat cgtctttgat    840

gatgccgatc ttgaaaaggc ggcagaaggg ctgattgctt caaaatatcg aaacgctggg    900
```

-continued

```
caaacttgtg tgtgtgccaa ccgtatctat gtccaaagtt caattaaaga tgagttttta    960

gcgaaattta aacaaaaagt agaagtactg aaagttggca atggtgctga tgaagcaacc   1020

gatatcggac cgcttatcaa tcaacaagca ctcaaaaaag tgcaggcact tttggatgat   1080

gcgctaaaca aaggggcaac gctaatcaca ggtggcgtgc cacatgacgc aagccaactg   1140

tcatttaccc caactgtcat cagtgatatc accgatgaga tggatcttgc ccatgaagag   1200

atatttggtc cgattgctcc gatcatgact tttgaagatg aaaaagaggt aatccatcgt   1260

gccaatgata ccatttatgg attggcggcg tatttttata cccaaagcca tgctcgtgct   1320

tggcgtgttt cagaggcact agagtatggt atggttggtc aaaatacagg gcttttatca   1380

actgaagttg caccatttgg tggtgttaag caatcaggtt ttgggcgaga gggttcaaaa   1440

tacggtattg aagagtatat tactaccaaa tattggtgta tggatatcag cgaata       1496


<210> SEQ ID NO 5
<211> LENGTH: 518
<212> TYPE: PRT
<213> ORGANISM: Moraxella catarrhalis

<400> SEQUENCE: 5

Met Ala Leu Lys Lys Ile Thr Gly Asn Leu Ser Ile Arg Arg Thr His
1               5                   10                  15

Met Ser Lys Pro Thr Leu Ile Lys Thr Thr Leu Ile Cys Ala Leu Ser
            20                  25                  30

Ala Leu Met Leu Ser Gly Cys Ser Asn Gln Ala Asp Lys Ala Ala Gln
        35                  40                  45

Pro Lys Ser Ser Thr Val Asp Ala Ala Ala Lys Thr Ala Asn Ala Asp
    50                  55                  60

Asn Ala Ala Ser Gln Glu His Gln Gly Glu Leu Pro Val Ile Asp Ala
65                  70                  75                  80

Ile Val Thr His Ala Pro Glu Val Pro Pro Pro Val Asp Arg Asp His
                85                  90                  95

Pro Ala Lys Val Val Val Lys Met Glu Thr Val Glu Lys Val Met Arg
            100                 105                 110

Leu Ala Asp Gly Val Glu Tyr Gln Phe Trp Thr Phe Gly Gly Gln Val
        115                 120                 125

Pro Gly Gln Met Ile Arg Val Arg Glu Gly Asp Thr Ile Glu Val Gln
    130                 135                 140

Phe Ser Asn His Pro Asp Ser Lys Met Pro His Asn Val Asp Phe His
145                 150                 155                 160

Ala Ala Thr Gly Pro Gly Gly Gly Ala Glu Ala Ser Phe Thr Ala Pro
                165                 170                 175

Gly His Thr Ser Thr Phe Ser Phe Lys Ala Leu Gln Pro Gly Leu Tyr
            180                 185                 190

Val Tyr His Cys Ala Val Ala Pro Val Gly Met His Ile Ala Asn Gly
        195                 200                 205

Met Tyr Gly Leu Ile Leu Val Glu Pro Lys Glu Gly Leu Pro Lys Val
    210                 215                 220

Asp Lys Glu Tyr Tyr Val Met Gln Gly Asp Phe Tyr Thr Lys Gly Lys
225                 230                 235                 240

Tyr Gly Glu Gln Gly Leu Gln Pro Phe Asp Met Glu Lys Ala Ile Arg
                245                 250                 255

Glu Asp Ala Glu Tyr Val Val Phe Asn Gly Ser Val Gly Ala Leu Thr
            260                 265                 270
```

-continued

```
Gly Glu Asn Ala Leu Lys Ala Lys Val Gly Glu Thr Val Arg Leu Phe
        275                 280                 285

Val Gly Asn Gly Gly Pro Asn Leu Thr Ser Ser Phe His Val Ile Gly
    290                 295                 300

Glu Ile Phe Asp Lys Val His Phe Glu Gly Gly Lys Gly Glu Asn His
305                 310                 315                 320

Asn Ile Gln Thr Thr Leu Ile Pro Ala Gly Gly Ala Ala Ile Thr Glu
                325                 330                 335

Phe Lys Val Asp Val Pro Gly Asp Tyr Val Leu Val Asp His Ala Ile
            340                 345                 350

Phe Arg Ala Phe Asn Lys Gly Ala Leu Gly Ile Leu Lys Val Glu Gly
        355                 360                 365

Glu Glu Asn His Glu Ile Tyr Ser His Lys Gln Thr Asp Ala Val Tyr
    370                 375                 380

Leu Pro Glu Gly Ala Pro Gln Ala Ile Asp Thr Gln Glu Ala Pro Lys
385                 390                 395                 400

Thr Pro Ala Pro Ala Asn Leu Gln Glu Gln Ile Lys Ala Gly Lys Ala
                405                 410                 415

Thr Tyr Asp Ser Asn Cys Ala Ala Cys His Gln Pro Asp Gly Lys Gly
            420                 425                 430

Val Pro Asn Ala Phe Pro Pro Leu Ala Asn Ser Asp Tyr Leu Asn Ala
        435                 440                 445

Asp His Ala Arg Ala Ala Ser Ile Val Ala Asn Gly Leu Ser Gly Lys
    450                 455                 460

Ile Thr Val Asn Gly Asn Gln Tyr Glu Ser Val Met Pro Ala Ile Ala
465                 470                 475                 480

Leu Ser Asp Gln Gln Ile Ala Asn Val Ile Thr Tyr Thr Leu Asn Ser
                485                 490                 495

Phe Gly Asn Lys Gly Gly Gln Leu Ser Ala Asp Asp Val Ala Lys Ala
            500                 505                 510

Lys Lys Thr Lys Pro Asn
        515

<210> SEQ ID NO 6
<211> LENGTH: 1556
<212> TYPE: DNA
<213> ORGANISM: Moraxella catarrhalis

<400> SEQUENCE: 6

atggcattga agaaaattac aggcaacctt tctataagga gaacccatat gtctaagcct     60

actttgataa aaacaacctt aatttgtgcc ttaagtgcat tgatgctcag tggttgtagc    120

aatcaagcgg acaaagccgc ccagccaaaa agcagcacgg tagacgctgc cgccaagaca    180

gcaaatgcag ataatgctgc ctcacaagaa catcaaggcg agctgcctgt cattgatgcc    240

attgttacgc atgcaccaga agttccacca cctgttgacc gtgaccaccc cgccaaagtg    300

gtggtaaaaa tggaaaccgt tgaaaaagtc atgcgtctgg cagatggcgt ggaatatcag    360

ttttggacat ttggcggtca agttccaggg cagatgattc gtgtgcgtga aggcgacacc    420

atcgaagtgc agttctcaaa ccacccagat tcaaaaatgc cccataatgt tgactttcac    480

gctgccacag ggcctggcgg cggggcagaa gcgtcattta ccgcaccggg tcatacatca    540

acctttagtt ttaaagcctt acagcctggt ttgtatgtct atcactgtgc ggttgcccct    600

gttggcatgc acattgctaa tggcatgtat ggtttgattt tggttgaacc aaaagagggc    660
```

-continued

```
ttgccaaaag tagataaaga atactatgtc atgcaaggcg acttttatac caaaggcaaa    720

tatggcgaac aaggtctaca gccctttgat atggaaaaag ccattcgaga agatgctgaa    780

tatgttgtct ttaatggttc ggtgggggcg ttgactggtg aaaatgctct aaaagccaag    840

gttggcgaaa ctgttcgctt atttgtgggt aacggcggcc cgaatttgac atcatcattc    900

catgtcattg gtgagatttt tgataaggtt cactttgagg gtggtaaggg tgaaaaccac    960

aatatccaaa ccacgctaat cccagcaggt ggcgctgcca tcactgaatt taaggtggat   1020

gtgccgggtg attatgtctt ggttgaccat gccatcttcc gtgcctttaa caaaggggca   1080

ttgggcatac ttaaggtgga aggtgaagaa aatcatgaga tttattcaca caaacaaaca   1140

gacgctgtct atctgccaga gggtgcccca caagcaattg atacccaaga agcacccaaa   1200

acacctgcac ctgccaactt acaagagcag attaaagcag gtaaggcaac ctatgactct   1260

aactgtgctg cttgtcacca acctgatggt aaaggcgtgc caaacgcttt cccaccgctt   1320

gccaactctg actatctgaa cgccgaccac gctcgtgccg ccagcatcgt ggcaaatgga   1380

ttgtctggta agattaccgt caatggcaac caatatgaaa gcgtcatgcc tgcgattgct   1440

ctgagcgacc aacagattgc caatgtcatc acctacacgc ttaacagctt tggtaacaaa   1500

ggcggtcaac tcagtgcaga cgatgtggca aaagccaaaa aaaccaagcc aaactg       1556
```

<210> SEQ ID NO 7
<211> LENGTH: 262
<212> TYPE: PRT
<213> ORGANISM: Moraxella catarrhalis

<400> SEQUENCE: 7

```
Met Ile Lys Pro Phe Ala Thr Leu Ala Thr Val Ala Cys Val Thr Leu
1               5                   10                  15

Ala Gly Cys Thr Lys Glu Glu Thr Ser Thr Gln Thr Thr Ala Pro Ala
            20                  25                  30

Gln Pro Ser Gln Lys Ser Ile Val Ile Ala Thr Glu Ala Ala Tyr Pro
        35                  40                  45

Pro Phe Asn Asp Thr Asp Ala Ser Gly Gln Ile Ile Gly Phe Asp Val
    50                  55                  60

Asp Val Met Asn Ala Leu Cys Ala Glu Met His Ala His Cys Gln Ile
65                  70                  75                  80

Ile Ala Gln Asp Trp Asp Gly Leu Ile Pro Ser Leu Leu Ala Gly Lys
                85                  90                  95

Tyr Asp Ala Ile Ile Ala Gly Met Ser Ile Thr Pro Glu Arg Gln Ala
            100                 105                 110

Gln Val Asp Phe Ser Asp Ser Tyr Phe Ser Asn Thr Ile Val Trp Leu
        115                 120                 125

Ala Lys Ser Asp Gly Ser Phe Asp Pro Asn Asn Ile Thr Asn Gln Thr
    130                 135                 140

Leu Ala Ser Gln Arg Gly Thr Thr Gly Ala Ala Tyr Ile Thr Glu Lys
145                 150                 155                 160

Tyr Asp Gly Lys Asp Gly Asn Arg Val Gln Leu His Asp Thr Tyr Thr
                165                 170                 175

Asn Ala Tyr Leu Asp Thr Lys Ala Gly Arg Asn His Ala Val Met Ala
            180                 185                 190

Glu Lys Val Ser Ala Ile Asp Trp Leu Lys Gln Glu Gly Asn Gly Glu
        195                 200                 205

Phe Gly Leu Ile Gly Glu Glu Ile Asp Asn Asn Asp His Leu Gly Ile
    210                 215                 220
```

-continued

```
Ala Val Arg Lys Gly Asp Ser Leu Lys Ala Glu Phe Asp Ala Ala Leu
225                 230                 235                 240

Ala Lys Ile Lys Glu Ser Gly Lys Leu Ala Glu Ile Glu Lys Ala His
                245                 250                 255

Phe Gln Ser Asp Thr Phe
            260


<210> SEQ ID NO 8
<211> LENGTH: 788
<212> TYPE: DNA
<213> ORGANISM: Moraxella catarrhalis

<400> SEQUENCE: 8

atgataaaac catttgccac tttggcaact gtcgcttgtg ttactttggc gggttgtacc      60

aaagaagaaa ccagcaccca aacaacagca cccgctcagc caagccaaaa aagcattgtg     120

atcgcaactg aagccgccta cccaccattt aatgacacgg atgccagcgg tcagattatc     180

ggttttgatg tggatgtgat gaatgcctta tgtgccgaaa tgcacgctca ctgtcagata     240

attgctcagg attgggatgg cttaatccca agcttattgg caggcaaata tgacgccatc     300

atcgcaggca tgtccatcac cccagagcgt caagcacaag tagatttttc ggactcttat     360

ttttcaaata cgatcgtttg gcttgccaaa agtgatggca gctttgatcc caataatatc     420

accaatcaaa cccttgccag tcagcgtggt actactggtg ctgcctatat caccgaaaaa     480

tatgatggta aagatggcaa tcgtgttcag ctgcatgaca cctacaccaa tgcttatttg     540

gacacaaaag caggacgcaa tcatgcagtc atggctgaaa aagtatcggc tattgactgg     600

ctaaagcaag agggcaatgg tgagtttggc ttaatcggcg aagagattga taataacgat     660

cacttgggta tcgccgtacg caaaggcgac agcctaaaag ctgagtttga tgcagcttta     720

gcaaaaatca aagaaagcgg taaattggca gaaattgaaa aagctcactt tcaatcagat     780

actttta                                                               788


<210> SEQ ID NO 9
<211> LENGTH: 189
<212> TYPE: PRT
<213> ORGANISM: Moraxella catarrhalis

<400> SEQUENCE: 9

Met Lys Leu Leu Lys Ile Thr Leu Phe Ala Ser Ile Leu Gly Ser Ala
1               5                   10                  15

Thr Phe Ser His Ser Leu Ser Ala Ile Ala Asn Thr Arg Phe Glu Thr
            20                  25                  30

Ile Asp Ile Thr Thr Leu Thr Asn Gln Ala Ala Arg Gly Asp Tyr His
        35                  40                  45

Ala Gln Phe Phe Leu Ala Lys Arg Leu Gln Lys Gly Glu Gly Val Thr
    50                  55                  60

Lys Asp Ala Ser Lys Ala Val Tyr Trp Tyr Thr Arg Ala Ala Glu Lys
65                  70                  75                  80

Asn Ile Ala Pro Ala Gln Leu Asn Leu Gly Ile Met Tyr Leu Arg Gly
                85                  90                  95

Glu Gly Val Arg Ala Asp Ile Ala Thr Gly Arg Ala Trp Leu Glu Lys
            100                 105                 110

Ala Ala Asn Leu Gly Asp Asn Arg Ala Ser Tyr Ala Leu Ala Met Ile
        115                 120                 125

Asp Glu Gln Gln Gln Arg Leu Val Asp Ala Tyr Lys Trp Tyr Asp Leu
```

-continued

```
    130                 135                 140

Ser Ala Arg Glu Gly Met Leu Asp Asp Asn Val Arg Asn Arg Ala Lys
145                 150                 155                 160

Val Lys Val Ser Gln Leu Ala Leu Asn Leu Ser Ser Ser Glu Ile Glu
                165                 170                 175

Ser Ala Lys Arg Ser Ala Asn Ala Trp Phe Leu Asn Gln
            180                 185


<210> SEQ ID NO 10
<211> LENGTH: 569
<212> TYPE: DNA
<213> ORGANISM: Moraxella catarrhalis

<400> SEQUENCE: 10

atgaaactgc ttaaaatcac cttatttgcc agcatattgg gcagtgccac tttcagtcat      60

tctctatccg ccattgctaa cactcgcttt gaaacaatcg atatcacaac cttgaccaat     120

caagccgctc gtggtgatta tcatgcccag tttttcttg ccaaacgctt gcaaaaagga      180

gaaggtgtta ccaaagacgc ctcaaaagct gtttattggt atacccgtgc cgccgaaaaa     240

aatattgctc cagctcagct caatcttggc atcatgtatt tgcgtggaga aggtgttaga     300

gccgatatag ccacaggccg agcttggctt gagaaagcag ccaatttggg ggataatcgt     360

gccagctatg ctttggcaat gattgatgag cagcaacaac gcttggttga tgcttataaa     420

tggtatgatt tatccgctcg tgagggtatg cttgatgata atgtacgcaa tcgtgctaag     480

gttaaagtca gccagcttgc tctgaattta tcctccagtg aaatcgaatc tgccaaacgc     540

agtgccaatg cgtggttttt aaatcagta                                       569


<210> SEQ ID NO 11
<211> LENGTH: 189
<212> TYPE: PRT
<213> ORGANISM: Moraxella catarrhalis

<400> SEQUENCE: 11

Met Lys Thr Val Ser Lys Ser Leu Leu Gly Leu Ala Ser Ile Thr Leu
1               5                   10                  15

Thr Ala Ser Leu Ser Met Asn Ala Gln Ala Gly Asn Ser Pro Ala Asn
            20                  25                  30

Ile Asp Asn Val Leu Gln Gln Leu Thr Thr Gln His Asn Asn Ala Ser
        35                  40                  45

Ser Leu Val Lys Ser Val Arg Gln Pro Ala Ser Leu Ala Leu Asn Ser
    50                  55                  60

Pro Met Ile Ala Gln Ser Thr Lys Ser Lys Lys Thr Asp Glu Asp Ile
65                  70                  75                  80

Pro Val Leu Asp Arg Leu Thr Ala Val Ala Ser Ser Thr Val Asn Lys
                85                  90                  95

Phe Lys Gln Asn Gly Ile Ala Ser Trp Tyr Gly Arg Gln Phe His Gly
            100                 105                 110

Arg Lys Thr Ala Ser Gly Glu Thr Phe Asp Met Asn Ala Leu Thr Ala
        115                 120                 125

Ala His Ser Ser Leu Pro Met Asn Cys His Val Arg Val Thr Asn Arg
    130                 135                 140

Asp Asn Gly Lys Ser Val Val Val Lys Ile Asn Asp Arg Pro Lys Thr
145                 150                 155                 160

Asn Arg Val Leu Asp Leu Ser Tyr Gly Ala Ala Gln Ala Ile Gly Met
                165                 170                 175
```

Thr Gly Asn Val Gly Asn Val Thr Ile Glu Arg Ile Asp
180 185

<210> SEQ ID NO 12
<211> LENGTH: 569
<212> TYPE: DNA
<213> ORGANISM: Moraxella catarrhalis

<400> SEQUENCE: 12
atgaaaacag tgagcaaatc tttacttgga ttagcgagca ttactttaac cgcaagttta 60
agcatgaatg cacaagctgg caatagccct gccaatatcg acaatgtact acagcagctc 120
accacgcagc ataataatgc gtcaagcttg gtcaaatcag tgcgtcaacc cgcctctttg 180
gcgcttaaca gtccaatgat tgctcaatcc accaaatcca aaaaaaccga tgaagatatt 240
cctgtgcttg accgtctgac cgcagtcgct tcaagcactg tcaataagtt caaacaaaat 300
ggcatcgctt catggtatgg tcgtcagttt catggtcgta aaactgccag tggcgaaacc 360
tttgatatga atgccttaac ggcagcacac agtagcctgc caatgaattg ccatgtcaga 420
gtgaccaatc gtgataatgg taaatctgtg gtcgtcaaaa tcaacgatcg acccaaaacc 480
aatcgtgtgc ttgatttgtc ttatggtgct gcccaagcca ttggtatgac tggtaatgtt 540
ggtaatgtaa ccattgagcg tattgatta 569

<210> SEQ ID NO 13
<211> LENGTH: 34
<212> TYPE: DNA
<213> ORGANISM: Artificial Sequence
<220> FEATURE:
<223> OTHER INFORMATION: Primer

<400> SEQUENCE: 13
atatatatcc atggaacagc tagggactgc cacc 34

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
tctctaggat ccagaaccac actggctggc catttc 36

<210> SEQ ID NO 15
<211> LENGTH: 20
<212> TYPE: DNA
<213> ORGANISM: Artficial Sequence

<400> SEQUENCE: 15
aacagctagg gactgccacc 20

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
cttcagggtc tgtccatatc tc 22

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
atatggatcc gcaagcctgt ttgattg 27

<210> SEQ ID NO 18
<211> LENGTH: 26
<212> TYPE: DNA
<213> ORGANISM: Artificial Sequence
<220> FEATURE:
<223> OTHER INFORMATION: Primer

<400> SEQUENCE: 18
gcgcgaattc ttattcgctg atatcc 26

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gatacacaca aggaagattt g 21

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
catagatacg gttggcacac ac 22

<210> SEQ ID NO 21
<211> LENGTH: 26
<212> TYPE: DNA
<213> ORGANISM: Artificial Sequence
<220> FEATURE:
<223> OTHER INFORMATION: Primer

<400> SEQUENCE: 21
atatggatcc agcggacaaa gccgcc 26

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
gcgcgaattc tcagtttggc ttggt 25

<210> SEQ ID NO 23
<211> LENGTH: 22
<212> TYPE: DNA
<213> ORGANISM: Artificial Sequence
<220> FEATURE:
<223> OTHER INFORMATION: Primer -continued

```
<400> SEQUENCE: 23

catttaccgc accgggtcat ac                                               22


<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24

cttcttgggt atcaattgct tg                                               22
```